(12) United States Patent
White et al.

(10) Patent No.: US 9,459,173 B2
(45) Date of Patent: Oct. 4, 2016

(54) SYSTEM AND METHOD FOR THREE DIMENSIONAL CALIBRATION OF FORCE PLATES

(71) Applicants: Bruce F. White, Boston, MA (US); Fred Ruland, Wayland, MA (US); Forest J. Carignan, Bedford, MA (US); Albert Drueding, Belmont, MA (US); Gary Glass, Newton, MA (US); Jonathan Taylor, Waltham, MA (US)

(72) Inventors: Bruce F. White, Boston, MA (US); Fred Ruland, Wayland, MA (US); Forest J. Carignan, Bedford, MA (US); Albert Drueding, Belmont, MA (US); Gary Glass, Newton, MA (US); Jonathan Taylor, Waltham, MA (US)

(73) Assignee: Advanced Mechanical Technology, Inc., Watertown, MA (US)

( * ) Notice: Subject to any disclaimer, the term of this patent is extended or adjusted under 35 U.S.C. 154(b) by 671 days.

(21) Appl. No.: 13/628,433

(22) Filed: Sep. 27, 2012

(65) Prior Publication Data

US 2013/0298633 A1 Nov. 14, 2013

Related U.S. Application Data

(63) Continuation-in-part of application No. 13/273,864, filed on Oct. 14, 2011, now Pat. No. 9,255,859.

(51) Int. Cl.
*G01L 25/00* (2006.01)
*A61B 5/00* (2006.01)
*A61B 5/103* (2006.01)
(Continued)

(52) U.S. Cl.
CPC ............. *G01L 25/00* (2013.01); *A61B 5/1036* (2013.01); *A61B 5/1038* (2013.01); *A61B 5/112* (2013.01); *A61B 5/4023* (2013.01); *A61B 5/6887* (2013.01); *A61B 5/7235* (2013.01); *G01G 23/01* (2013.01); *G01L 5/16* (2013.01); *A61B 5/1116* (2013.01); *A61B 2560/0223* (2013.01); *A61B 2562/0247* (2013.01)

(58) Field of Classification Search
CPC ....... G01L 5/16; G01L 5/0028; G01L 25/00; A61B 2560/0223; A61B 2562/0247; A61B 5/1036; A61B 5/1038; A61B 5/6887; G01G 23/01; G01G 25/00
See application file for complete search history.

(56) References Cited

U.S. PATENT DOCUMENTS 5,355,715 A    10/1994  Rausche et al.
5,814,740 A *   9/1998  Cook ...................... G01L 5/164
                                              73/862.637
(Continued)

OTHER PUBLICATIONS

Bartel et al., Force Measurement Services at NIST—Equipment, Procedures, and Uncertainty, NCSL Workshop and Symposium, 1997.*

(Continued)

*Primary Examiner* — Gregory J Toatley, Jr.
*Assistant Examiner* — Kyle R Quigley
(74) *Attorney, Agent, or Firm* — AKC Patents LLC

(57) ABSTRACT

A method for calibrating a force platform includes, providing a force platform and applying an n×m grid on a top surface of the force platform via a computing device. Next, applying p known loads on each of the n×m grid points of the top surface along a Z-axis being perpendicular to the X and Y axes and along the X and Y axes. Next, taking multipoint measurements at each grid point and for each applied known load along the X, Y and Z axes and generating six measured output signals, exact position coordinates and applied known load magnitude for each grid point. Next, assembling an array of n×m×p of six equations with six unknown for each grid point and applied known load and then solving the assembled equations and deriving a position and load specific calibration matrix for each grid point.

17 Claims, 17 Drawing Sheets

(51) Int. Cl.
*G01G 23/01* (2006.01)
*G01L 5/16* (2006.01)
*A61B 5/11* (2006.01)

(56) References Cited

U.S. PATENT DOCUMENTS

| | | |
|---|---|---|
| 6,159,761 A | 12/2000 | Okada |
| 6,389,883 B1 | 5/2002 | Berme et al. |
| 6,532,830 B1 | 3/2003 | Jansen |
| 7,059,202 B2 | 6/2006 | Stanos et al. |
| 7,918,143 B2 | 4/2011 | Meyer et al. |
| 8,006,575 B2 | 8/2011 | Metzger |
| 8,156,823 B2 | 4/2012 | Kim et al. |
| 2002/0104366 A1* | 8/2002 | Sinnett ............... G01M 17/022 73/1.01 |
| 2008/0005049 A1 | 1/2008 | Wheeler |
| 2008/0179111 A1 | 7/2008 | Jwo |
| 2009/0107207 A1* | 4/2009 | Yamazaki ............. G01G 23/01 73/1.13 |

OTHER PUBLICATIONS

Collins et al., A simple method for calibrating force plates and force treadmills using an instrumented pole, NIH-PA, Aug. 27, 2008.*
Huijing Wang et al. 'Measuring system of a 3D force platform for plantar pressure distribution', Proceedings of the IEEE International Conference on Automation and Logistics Shenyang, China, Aug. 2009, Aug. 7, 2009. pp. 906-910.

* cited by examiner

SYSTEM AND METHOD FOR THREE DIMENSIONAL CALIBRATION OF FORCE PLATES

CROSS REFERENCE TO RELATED CO-PENDING APPLICATIONS

This application is a continuation in part and claims the benefit of U.S. application Ser. No. 13/273,864 filed on Oct. 14, 2011 and entitled FORCE PLATFORM SYSTEM which is commonly assigned and the contents of which are expressly incorporated herein by reference.

FIELD OF THE INVENTION

The present invention relates to a system and a method for three dimensional calibration of force plates, and more particularly to a three dimensional calibration of force plates that provides improved measurement accuracy and reduction of crosstalk errors.

BACKGROUND OF THE INVENTION

A force platform is a measuring device that measures ground reaction forces. Typically force platforms are mounted in a pit so that their top surface lies flush with the floor. Subjects are then instructed to walk across or stand on the platforms and the generated ground reaction forces are recorded. Force platforms are commonly used for research and clinical studies in biomechanics, medical research, orthopedics, rehabilitation evaluation, prosthetic uses and engineering, among others. In one example, a force platform is used to measure the amount of sway in a person's stance while the person stands on the platform. Force platforms accomplish this by measuring three orthogonal force components (Fx, Fy, Fz) along the x, y and z axes as well as moments (Mx, My, Mz) about those axes.

Force platform systems usually include a force plate, multi-axis spring members upon which a series of strain gauges are fixed for sensing loads along multiple axes, an amplifier or signal conditioner, either connected to or embedded in the force plate or platform, and a computer for data collection. Electrical signals from the strain gauges are transmitted to the amplifier which amplifies the signals to a sufficient voltage for processing in the computer. Data collection can be either digital or analog depending on the medium chosen. In other embodiments, piezoelectric sensors, Hall effect sensors, optical sensors, capacitors or mechanical sensors are used to measure loads along multiple axes of the platform.

Both the force plate and the signal conditioner require calibration to accurately convert raw data to usable data. Furthermore, a high degree of sensitivity and accuracy is needed in the sensing and transmission of strain signals. As was mentioned above, force platforms are designed to produce multiple channel outputs corresponding to six possible loads, i.e., three orthogonal force components (Fx, Fy, Fz) along the x, y and z axes and three moments (Mx, My, Mz) about those axes. However, small imperfections in the manufacturing and design of the force platform result in slight off-axis sensitivity. In one example, off-axis sensitivity causes the output signal in the Fx channel to be slightly sensitive to a force load Fz applied along the z-direction. This off-axis sensitivity causes the sensing and transmission of erroneous signals, which are commonly referred to as crosstalk errors. Cross talk errors usually result in inaccurate measurements.

Accordingly, there is a need for an improved system and method for calibrating a force plate that corrects for the crosstalk errors.

SUMMARY OF THE INVENTION

The present invention addresses the force plate calibration problem and provides a system and a method for calibrating a force plate with improved accuracy.

In general, in one aspect, the invention features a method for calibrating a force platform including the following. Providing a force platform and applying an n×m grid on a top surface of the force platform via a computing device. The n×m grid comprises n points along an X-axis, and m points along a Y-axis of the force platform. Next, applying p known loads on each of the n×m grid points of the top surface along a Z-axis being perpendicular to the X and Y axes and along the X and Y axes. Next, taking multipoint measurements at each grid point and for each applied known load along the X, Y and Z axes and generating six measured output signals, exact position coordinates and applied known load magnitude for each grid point. Next, assembling an array of n×m×p of six equations with six unknown for each grid point and applied known load. Next, solving the assembled equations and deriving a position and load specific calibration matrix for each grid point. Finally, entering the derived position and load specific calibration matrices for all grid points in a calibration table and storing the calibration table in a non-volatile memory.

Implementations of this aspect of the invention may include one or more of the following features. The p known loads are applied via a 3-D Cartesian load apparatus. The applied p known loads comprise magnitudes in the range of zero to Full Scale Capacity (FSC) at increments of 10%. The n and m points comprise values in the range of 2 to 20. The six measured output signals comprise three force components Fx, Fy, Fz and three moment components Mx, My, Mz. The method further includes providing an estimate algorithm and storing a global platform calibration matrix in the non-volatile memory. The estimate algorithm is configured to generate first estimates of magnitude and position of an unknown applied load on the force platform by applying the global platform calibration matrix onto measured platform outputs for the unknown applied load. The first estimates of magnitude and position of the unknown applied load are used to determine a position and load specific calibration matrix in the calibration table. The method further includes generating accurate measures of the magnitude and position of the applied unknown load by applying the determined position and load specific calibration matrix onto the measured platform outputs for the unknown load. The method further includes verifying the derived position and load specific calibration matrices by applying NIST traceable dead weights onto the top surface grid points. The method further includes measuring secondary characteristics at eight grid points using a ten point up and a ten point down calibration protocol.

In general, in another aspect, the invention features a system for calibrating a force platform including a force platform, a computing device, a 3-D Cartesian load apparatus, a sensor, an algorithm, and a non-volatile memory. The computing device is configured to apply an n×m grid on a top surface of the force platform. The n×m grid has n points along an X-axis, and m points along a Y-axis of the force platform. The 3-D Cartesian load apparatus is configured to apply p known loads on each of the n×m grid points of the top surface along a Z-axis being perpendicular to the X and Y axes and along the X and Y axes. The sensor is configured to take multipoint measurements at each grid point and for each applied known load along the X, Y and Z axes and to generate six measured output signals, exact position coordinates and applied known load magnitude for each grid point. The algorithm is used for solving an assembled array of n×m×p of six equations with six unknown for each grid point and applied known load and for deriving a position and load specific calibration matrix for each grid point. The non-volatile memory is configured to store a calibration table comprising the derived position and load specific calibration matrices for all grid points.

Implementations of this aspect of the invention may include one or more of the following features. The applied p known loads comprise magnitudes in the range of zero to Full Scale Capacity (FSC) at increments of 10%. The n and m points comprise values in the range of 2 to 20. The six measured output signals comprise three force components Fx, Fy, Fz and three moment components Mx, My, Mz. The system further includes an estimate algorithm and a global platform calibration matrix. The estimate algorithm is configured to generate first estimates of magnitude and position of an unknown applied load on the force platform by applying the global platform calibration matrix onto measured platform outputs for the unknown applied load. The first estimates of magnitude and position of the unknown applied load are used to determine a position and load specific calibration matrix in the calibration table. The system further includes a correction algorithm generating accurate measures of the magnitude and position of the applied unknown load by applying the determined position and load specific calibration matrix onto the measured platform outputs for the unknown load.

In general, in another aspect, the invention features a calibrated force platform including a non-volatile memory storing a calibration table comprising position and load specific calibration matrices.

Implementations of this aspect of the invention may include one or more of the following features. The position and load specific calibration matrices correspond to n×m grid points of a top surface of the force platform and p known loads applied along an axis perpendicular to the top surface. The calibrated force platform further includes a global calibration matrix. The calibrated force platform further includes an estimate algorithm configured to generate a first estimate of an unknown applied load and position coordinates on the force platform by applying the global calibration matrix onto measured platform outputs. The first estimate of the unknown applied load and position coordinates are used to identify a position specific calibration matrix in the calibration table. The calibrated force platform further includes a correction algorithm configured to generate accurate measures of the applied unknown load magnitude and position coordinates by applying the identified position specific calibration matrix onto the measured platform outputs.

Among the advantages of this invention may be one or more of the following. The calibration process of this invention improves the accuracy of the force platform measurements, as shown in FIG. 12A-FIG. 12F. The typical cross talk error is in the order of ±0.01% of the applied load, and the typical load error is less than 0.001 or ±0.1% of applied load. The average Center of Pressure (COP) error is typically less than 0.2 mm.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views.

DETAILED DESCRIPTION OF THE INVENTION

Figure 1:
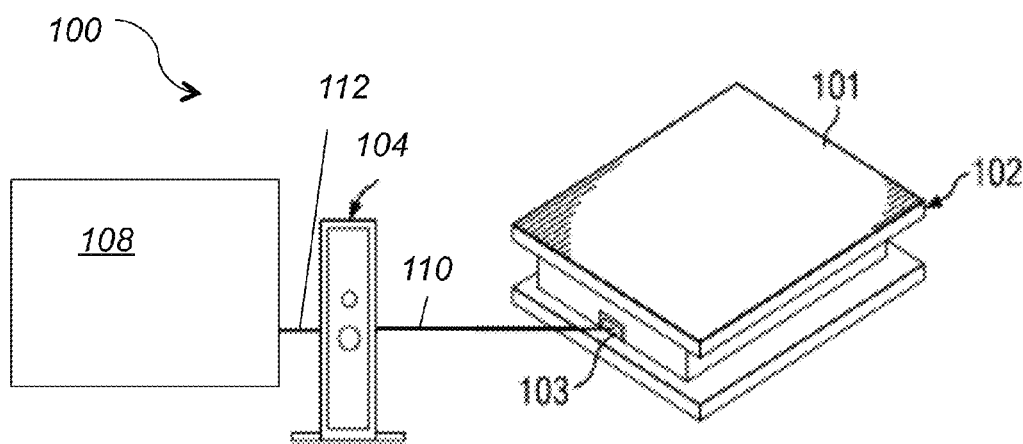
FIG. 1 illustrates an overview diagram of a force platform system.

FIG. 1 is an illustration of a force platform system 100 according to an embodiment of the invention. System 100 is used to measure ground reaction forces and includes a force platform 102, a signal conditioner 104, and a computer 108 used for data collection. The system may include more than one force platforms, and/or signal conditioners. Signal conditioner 104 may be an analog amplifier and/or digital processor, and may be connected to or embedded in the force plate. Computer 108 may be a personal computer (PC), a server, a mobile computing device or a computing circuit.

Force platform 102 shown in FIG. 1 is designed to measure the forces and moments applied to its top surface 101 as a subject stands, steps, or jumps on it. Force platform 102 outputs force signals to output port 103, where platform 102 can connect to and communicate with force signal conditioner 104.

Figure 2:
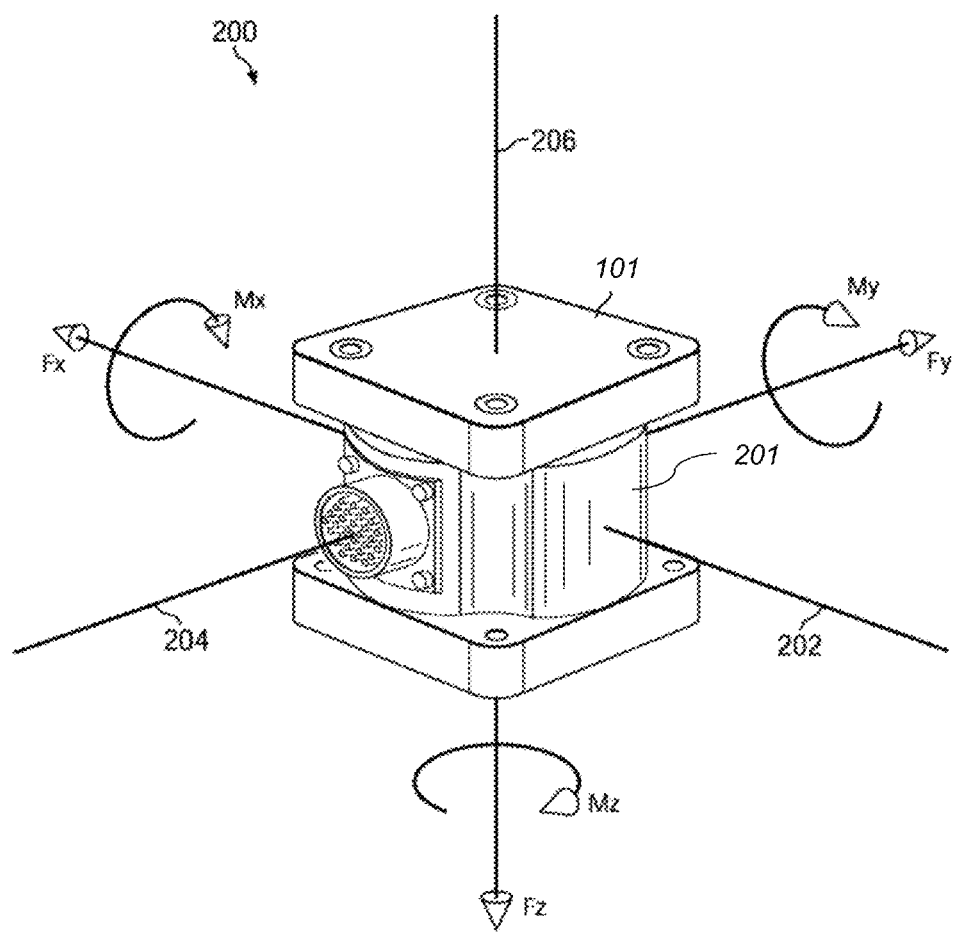
FIG. 2 depicts a transducer and the three forces and three moment components that are measured with the transducer.

Force platform 102 includes one or more force transducers or load cells for measuring forces. FIG. 2 shows the three force components Fx, Fy, and Fz and the three moment components Mx, My and Mz that are measured by a force transducer 201 as a subject is in contact with platform 200. Fx, Fy, and Fz are the force components that act along the axes 202, 204, and 206 of an orthogonal x, y, and z-coordinate system. In FIG. 2, the arrows point in the direction of positive force along each of the axes, following the right-hand rule. Fx and Fy are the horizontal or shear force components, and Fz is the vertical force component. Mx, My and Mz are the three torque and moment components. The torque and moments rotate around the corresponding x, y and z axes 202, 204, and 206, respectively. Positive moments are determined according to the right hand rule. When looking down an axis (in its positive direction) positive moments have a clockwise rotation.

Referring back to FIG. 1, amplifier or signal conditioner 104 is connected to force plate 102. For each of the three forces Fx, Fy, Fz and the three moment Mx, My, Mz components that are measured, the signal conditioner 104 supplies an excitation voltage to a set of strain gauge bridges embedded in the force platform 102. The resulting output is a low level voltage proportional to that component of the applied mechanical load. This output can be sampled by the signal conditioner 104, and various signal conditioning techniques may be applied. The signal conditioner 104 provides digital and/or analog data streams to the connected computer 108.

The signal conditioner 104 connects to computer 108 through some sort of medium, such as an analog card, a Universal Serial Bus (USB), an Ethernet or a serial interface (not shown). In the example of FIG. 1, signal conditioner 104 is connected via a USB connection 112 to a single computer 108. When the computer 108 receives the ground reaction force data, it performs additional processing and displays or saves the data depending on the software program.

Figure 3A:
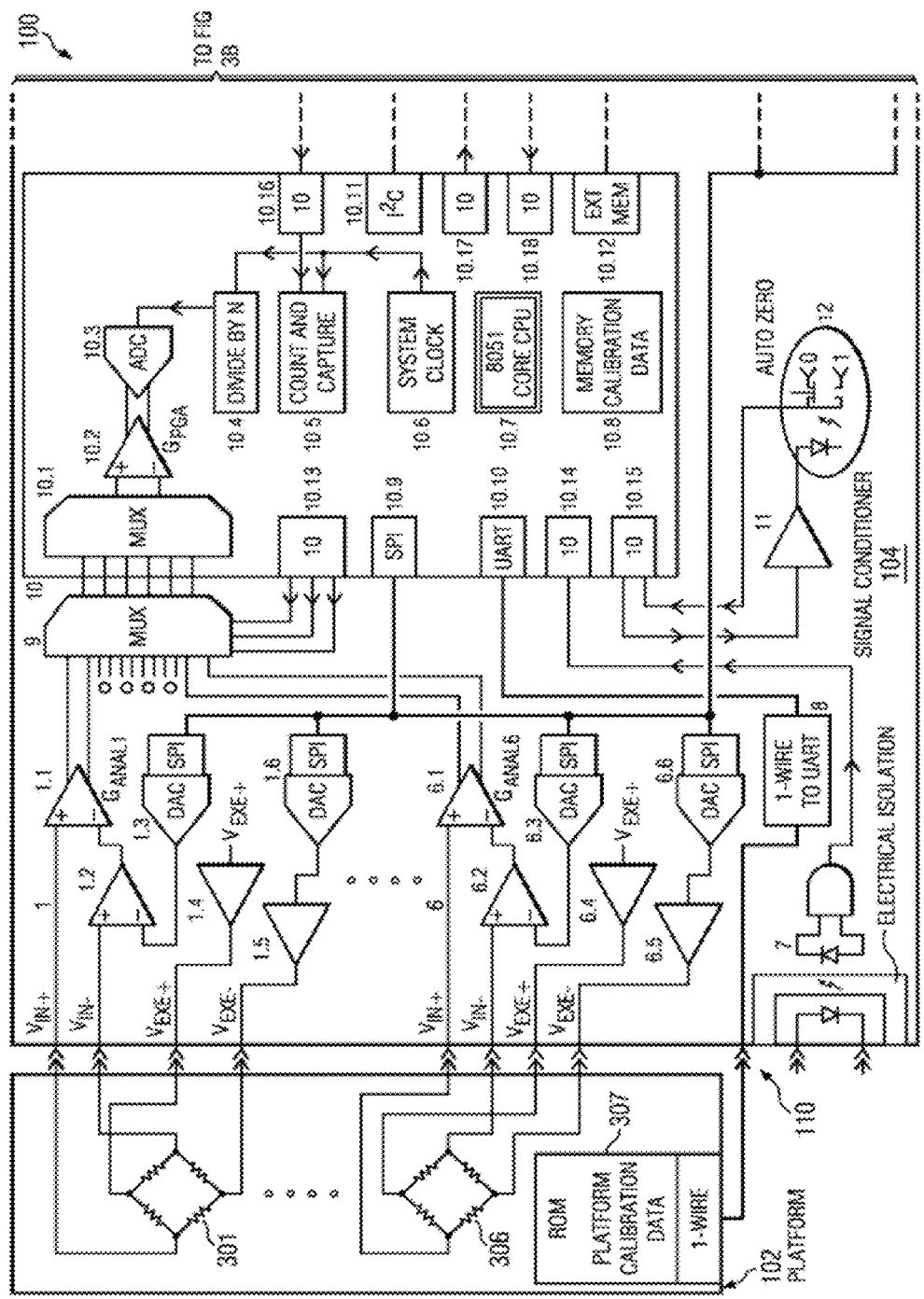
FIG. 3A and FIG. 3B depict the hardware architecture of the system of FIG. 1.
Figure 3B:
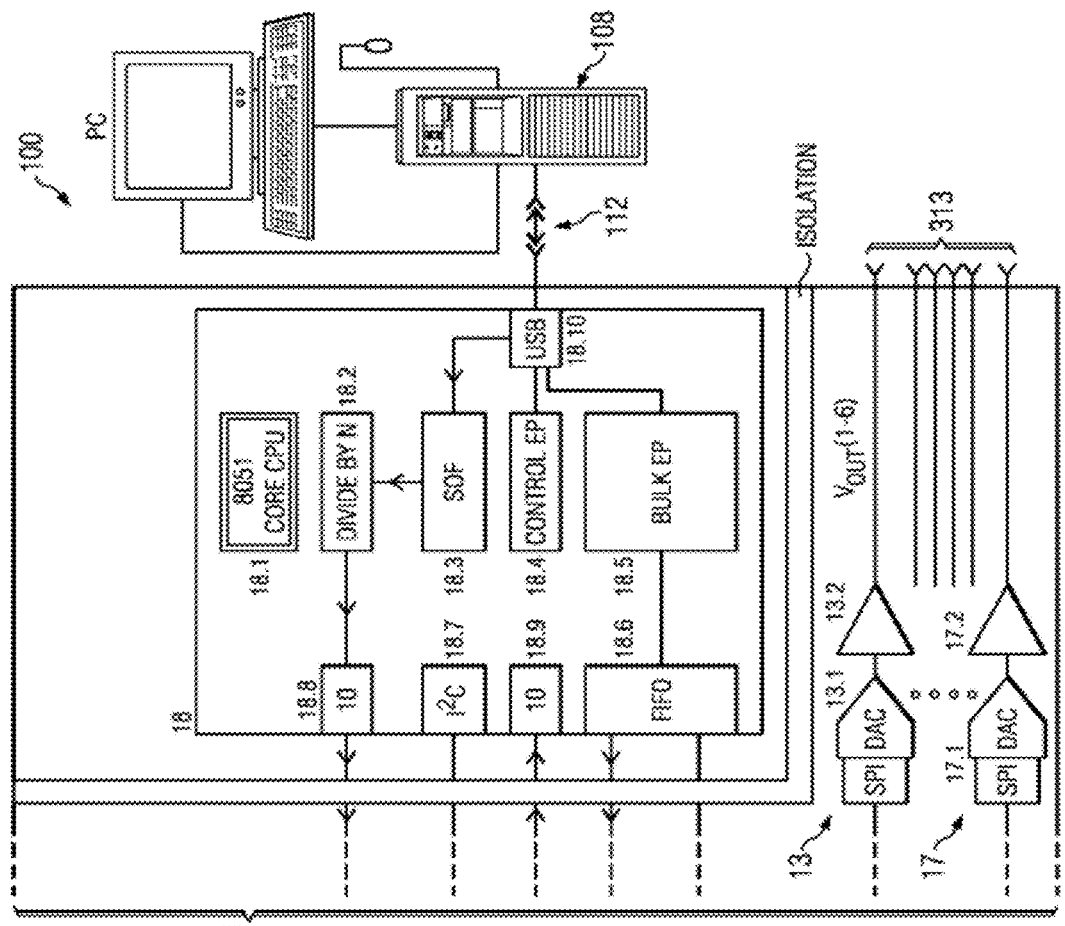

FIG. 3A and FIG. 3B illustrate the hardware architecture of an embodiment of a force platform system 100 including force platform 102, signal conditioner 104, and computer 108. Force platform 102 is connected to signal conditioner 104 via connection or cable 110, which includes connections for excitation voltages $V_{ExE+}$, $V_{ExE-}$ and output voltages $V_{IN+}$ and $V_{IN-}$ for multiple channels of force signals. In the example of FIG. 3A, platform 102 includes six force channels associated with six strain gauges, each including a bridge circuit 301-306 driven by excitation voltages $V_{ExE+}$, $V_{ExE-}$ and providing bridge output voltages $V_{IN+}$ and $V_{IN-}$. For simplicity, only circuitry for force channels 1 and 6, including strain gauges 301 and 306 in platform 102 and amplifiers 1 and 6 in signal conditioner 104, are shown in FIG. 3A. The omitted circuitry for channels 2-5 is identical to that shown for channels 1 and 6.

Connection or cable 110 may also include a communication link, such as a 1-Wire interface, to allow signal conditioner 104 to retrieve data stored in nonvolatile memory 307 of platform 102. Nonvolatile memory 307 may be read only memory (ROM) as shown in FIG. 3A, or may be programmable, including reprogrammable, memory, such as an EPROM. Nonvolatile memory 307 stores force platform calibration data and may also store a platform serial number and platform capacity.

As shown in FIG. 3B, signal conditioner 104 is connected to PC 108 via a USB connection 112. A primary function of signal conditioner 104 is to condition force data from multiple strain gauge inputs and output the results as multiple analog channels and/or a multiple channel digital data stream. The analog outputs may be high level and suitable as inputs to a multi-channel analog-to-digital converter (ADC). The digital data output may be transmitted to a host PC 108 via USB connection 112. The USB connection 112 may also be used to send and receive control and status information used by signal conditioner 104. It will be understood that additional signal conditioners 104 may be connect via USB to computer 108. Signal conditioner 104 receives commands and timing signals from the host PC 108 and sends digital force signals to the PC 108 via the USB connection 112. Alternatively or in addition, signal conditioner 104 outputs analog force signals, illustrated in FIG. 3B as $V_{OUT\,(1-6)}$, at an analog output port 313, which may be further connected to an input port (not shown) of computer 108 for receiving analog signals.

FIG. 3A and FIG. 3B illustrate further details of the hardware components of signal conditioner 104. Signal conditioner 104 includes a microprocessor 10 for digitizing and conditioning the force signals received from platform 102 and a microprocessor 18 for communicating with PC 108 via a USB connection 112. Microprocessor 10 is connected to and communicates with microprocessor 18 via communication lines that include an I2C bus interface 10.11, an 8-bit extended memory interface 10.12, a 1-bit SOF to Count-and-Capture line 10.16, a 1-bit microprocessor to USB interface bus 10.17, and a 3-bit unidirectional asynchronous bus 10.18. Microprocessor 10 is connected to and communicates with other components of signal conditioner 104 via a Serial Peripheral Interface (SPI) bus. The SPI bus connects to microprocessor 10 at SPI Bus interface 10.9.

The signal conditioner 104 includes, for force channel 1, an analog signal conditioning circuitry 1 that is connected to the bridge circuitry of strain gauge 301 and includes a differential amplifier 1.1. One input to differential amplifier 1.1 is the bridge output voltage $V_{IN+}$ and another input is a bridge balancing voltage that is provided by the signal conditioning circuitry 1. Differential amplifier 1.1 has a gain $G_{ANAL1}$ and an output that is connected to a multiplexer 9. A differential amplifier 1.2 is connected between strain gauge 301 and differential amplifier 1.1 for inserting the bridge balancing voltage into force channel 1. A digital-to-analog converter (DAC) 1.3 is used to produce the bridge balancing voltage under the control of microprocessor 10. One input of differential amplifier 1.2 is connected to the output of DAC 1.3; the other input of amplifier 1.2 is connected to strain gauge 301 to receive the bridge output voltage $V_{IN-}$ from strain gauge 301. The signal conditioning circuitry 1 also includes a power amplifier 1.4 connected to strain gauge 301 for supplying the positive bridge excitation voltage $V_{ExE+}$ to strain gauge 301. Also included is a power amplifier 1.5 connected to strain gauge 301 for providing a negative bridge excitation voltage $V_{ExE-}$ to strain gauge 301. A DAC 1.6 connected to the input of power amplifier 1.5 is used to produce the negative bridge excitation voltage $V_{ExE-}$ under the control of microprocessor 10. Both DAC 1.3 and DAC 1.6 are connected to the SPI Bus interface 10.9 of microprocessor 10.

As shown in FIG. 3A, the analog signal conditioning circuitry 6 for force channel 6 includes identical components to signal conditioning circuitry 1 for force channel 1. Conditioning circuitry 6 is connected to strain gauge 306 and includes a differential amplifier 6.1, a differential amplifier 6.2, a DAC 6.3, a power amplifier 6.4, a power amplifier 6.5, and a DAC 6.6. As with amplifier 1.1, differential amplifier 6.1 has a gain $G_{ANAL6}$ and an output connected to multiplexer 9. Similarly, both DAC 6.3 and DAC 6.6 are connected to microprocessor 10 via an SPI bus connection. Like circuitry is provided for each channel but not shown.

Multiplexor 9 is a 6-to-3 differential line multiplexor that receives the six force channels from the signal conditioning circuitries 1 through 6 and multiplexes the six channels into three differential output lines that are connected to microprocessor 10. Multiplexor 9 receives inputs, e.g., control signals, from microprocessor 10 via a 3-bit bus connection.

In the example shown in FIG. 3A, microprocessor 10 is a SILICON LABORATORIES (Silab) 8051 based mixed-signal microcontroller that comprises multiple components, including a system clock 10.6, e.g., with a nominal clock rate of 100 MHz, a 8051 based core CPU 10.7, system nonvolatile memory 10.8, e.g., for storing calibration and configuration data, and various interfaces and inputs/outputs to communicate with external circuitry. The components of microprocessor 10 are interconnected to allow for communication among the components and with CPU 10.7. For simplicity, only some of the interconnections are shown in FIG. 3A.

Microprocessor 10 receives inputs, i.e., force signal inputs, from external multiplexor 9 via a 3-line-to-1-line differential multiplexor 10.1. In turn, microprocessor 10 communicates with external multiplexor 9 via a 3-bit bus interface 10.13. A programmable Gain Amplifier 10.2 having gain $G_{PGA}$ connects the output of multiplexor 10.1 to the input of a 12-bit differential input analog-to-digital converter (ADC) 10.3. Signal conditioner 104 amplifies the multiplexed analog force signal received from the signal conditioning circuitries 1 through 6 using amplifier 10.2 and converts the amplified signal to digital signals using ADC 10.3. The digitized force signals are then available for further processing, such as conditioning the signals based on calibration data. Calibration data include calibration data retrieved from the nonvolatile memory 307 of force platform 102 and may also include signal conditioning calibration data stored in nonvolatile memory 10.8 of microprocessor 10.

Referring back to FIG. 2, the force components that act along the axes of the force plate's orthogonal x, y, and z coordinate system are designated Fx, Fy, and Fz. The moment and torque components which rotate around each force axis are designated Mx, My and Mz. Force platform 102 provides six channels of output. Each channel represents one of the six components of the applied load, i.e., the three orthogonal forces and the three orthogonal moments and torques. Crosstalk occurs when some portion of applied load to one channel appears in the output of another. This residual output is caused by the mechanical/electrical limitations of the measuring device and can be corrected for. This is done by applying known force, moments and torques to each platform 102 at key positions and recording the output across all channels. From this output a 6 by 6 calibration matrix is derived (see Table 1 below). In Table 1, Fx, Fy, Fz, Mx, My, Mz represent the applied load components and VFx, VFy, VFz, VMx, VMy, VMz are the measured values. This matrix (also referred to as sensitivity matrix) is then used to both convert the output from each channel into engineering units and to correct for crosstalk.

TABLE 1

Sample Calibration Matrix

Sample Calibration Matrix Channel

| | 0<br>VFx | 1<br>VFy | 2<br>VFz | 3<br>VMx | 4<br>VMy | 5<br>VMz |
|---|---|---|---|---|---|---|
| | Input to channel i(lb, in-lb) is B(l, j)<br>times the electrical output: j(uV, Vex)<br>BP 400600-2000 | | | | | |
| Fx | 0.6519 | −0.0068 | −0.0019 | 0.0009 | −0.0017 | −0.0003 |
| Fy | 0.0090 | 0.6515 | −0.0037 | 0.0009 | 0.0008 | 0.0010 |
| Fz | 0.0018 | 0.0017 | 2.5523 | −0.0062 | 0.0001 | 0.0026 |
| Mx | −0.0044 | −0.0032 | 0.0003 | 12.8281 | 0.0108 | −0.0138 |
| My | 0.0725 | −0.0032 | 0.0003 | 0.0058 | 10.1358 | −0.0140 |
| Mz | 0.0649 | 0.0821 | 0.0792 | 0.0123 | 0.0340 | 5.4451 |

Platform 102 in the force platform system 100 stores a platform identification and calibration matrix in non volatile memory 307 (see FIG. 3A). When a force platform 102 is connected to a signal conditioner 104 the calibration matrix becomes available to the signal conditioner 104, which stores its own calibration settings in non volatile memory (see FIG. 3A, memory 10.8). In other embodiments, the calibration data may be programmable and retrievable by external electronics, e.g., signal conditioner 104.

When recording data, the signal conditioner 104 reads mV inputs from each platform output channel, and converts them to engineering units. When doing this the signal conditioner 104 uses calibrated gains and excitations, and provides crosstalk corrections by applying the calibration matrix. The signal conditioner 104 digital output stream to the PC 108 consists of fully processed IEEE floating point numbers presented in their respective engineering units.

The signal conditioner 104 performs extensive numerical processing which includes: using factory calibrated constants in place of nominal values for gains and excitations, correcting for cable losses due to finite bridge resistances, and providing crosstalk corrections by applying a factory calibrated platform correction matrix. Signal conditioner 104 may also remove a DC offset, implement a user defined DC set point, and perform rotational transformation to compensate for physical platform placement considerations.

Figure 5:
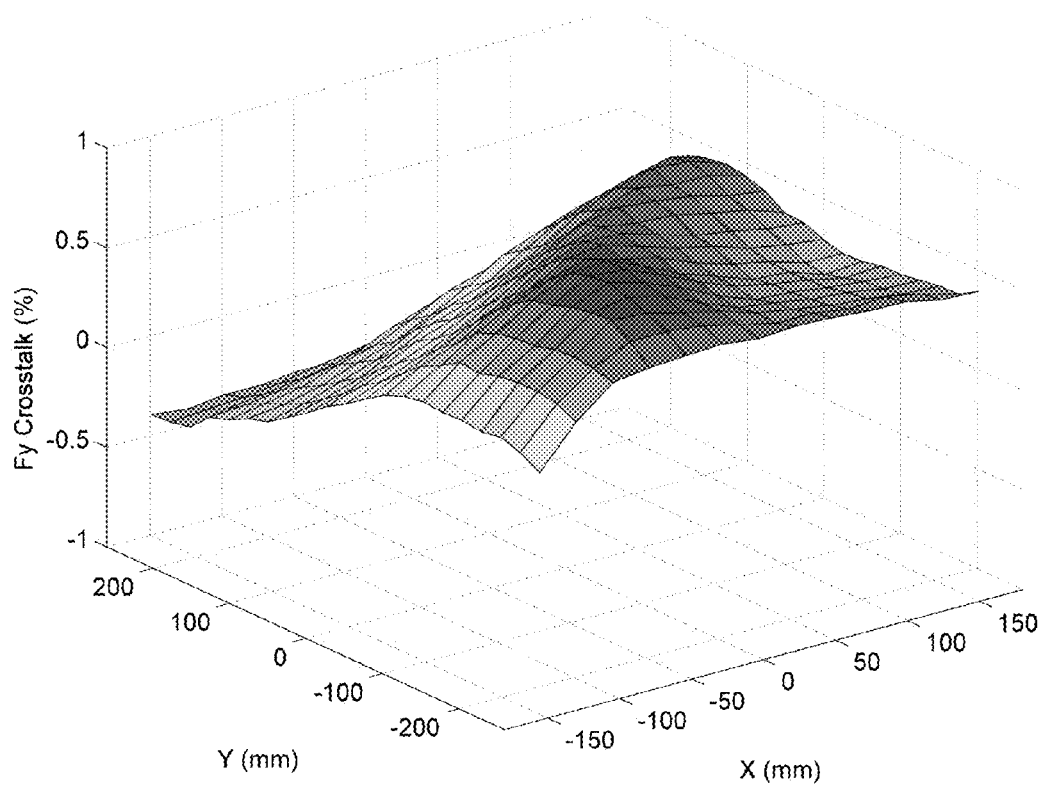
FIG. 5 depicts typical prior art crosstalk error distribution for Fy.

Prior art calibration procedures involve loading the force platform at a limited number of location points with known loads and taking the strain gauge readings. At least six locations are needed in order to generate six equations with the six unknown sensitivities of the calibration matrix. The six equations are solved for the six unknown sensitivities of the calibration matrix and the resulting single ("global") calibration matrix is used to calculate the applied forces on the entire surface area of the force platform. The resulting cross talk error distribution on the surface area of the force platform is shown in FIG. 5. As shown in FIG. 5, cross-talk errors of the order of 1% are observed across the surface area of the force platform with this prior art calibration procedure. This type of accuracy is usually not acceptable for diagnostic purposes. Therefore, there is a need for an improved calibration procedure that reduces the cross-talk errors to less than 1% across the surface area of the force platform.

In a typical prior art calibration procedure, known forces are applied at different spatial locations on the platform surface and six output signals are measured. The six signals represent the three force components $vf_x$, $vf_y$, $vf_z$ and the three moment components $vm_x$, $vm_y$, $vm_z$. The following equation (1) represents the relationship between the six measured outputs including three force components $vf_x$, $vf_y$, $vf_z$ and three moment $vm_x$, $vm_y$, $vm_z$ components with the three applied forces $f_x$, $f_y$, $f_z$ and the three total moments $M_x$, $M_y$, $M_z$, respectively:

$$vf_x = S_{fx} f_x$$

$$vf_y = S_{fy} f_y$$

$$vf_z = S_{fz} f_z$$

$$vm_x = S_{mx}(T_x + m_x) = S_{mx} M_x$$

$$vm_y = S_{my}(T_y + m_y) = S_{my} M_y$$

$$vm_z = S_{mz}(T_z + m_z) = S_{mz} M_z \quad \text{Equation (1)}$$

The total moments $M_x$, $M_y$, $M_z$ are the sums of the applied torques $T_x$, $T_y$, $T_z$ around axes x, y, z, respectively, and the applied moments of forces $m_x$, $m_y$, $m_z$ around axes x, y, z, respectively. The proportionality factors $S_{fx}$, $S_{fy}$, $S_{fz}$, $S_{mx}$, $S_{my}$, $S_{mz}$ are the "global" calibration sensitivity terms. The calibration procedure involves applying known forces and known moments and solving for the sensitivity terms.

Another indirect measurement involves the X and Y coordinates of the center of pressure (COP) location. The COP is the point where a single force vector may be applied in order to generated the distributed forces applied by the subject's foot (or other contacting element) onto the force platform surface. The X and Y coordinates of the COP are determined according to the following equation:

$$COPx = X_{cop} = m_y / f_z$$

$$COPy = Y_{cop} = m_x / f_z \quad \text{Equation (2)}$$

Equation (1) does not take into consideration the crosstalk terms. A general equation that takes crosstalk into consideration is shown in Equation (3) below:

$$v_1 = s_{11} f_1 + s_{12} f_2 + s_{13} f_3 + s_{14} f_4 + s_{15} f_5 + s_{16} f_6$$

$$v_2 = s_{21} f_1 + s_{22} f_2 + s_{23} f_3 + s_{24} f_4 + s_{25} f_5 + s_{26} f_6$$

$$v_3 = s_{31} f_1 + s_{32} f_2 + s_{33} f_3 + s_{34} f_4 + s_{35} f_5 + s_{36} f_6$$

$$v_4 = s_{41} f_1 + s_{42} f_2 + s_{43} f_3 + s_{44} f_4 + s_{45} f_5 + s_{46} f_6$$

$$v_5 = s_{51} f_1 + s_{52} f_2 + s_{53} f_3 + s_{54} f_4 + s_{55} f_5 + s_{56} f_6$$

$$v_6 = s_{61} f_1 + s_{62} f_2 + s_{63} f_3 + s_{64} f_4 + s_{65} f_5 + s_{66} f_6 \quad \text{Equation (3)}$$

Terms v1-v6 are equivalent to terms $vf_x$, $vf_y$, $vf_z$, $vm_x$, $vm_y$, $vm_z$ in equation (1). Similarly, terms f1-f6 are equivalent to terms $f_x$, $f_y$, $f_z$, $M_x$, $M_y$, $M_z$ in equation (1). Equation (3) is rewritten in matrix form as follows:

$$\begin{vmatrix} v_1 \\ v_2 \\ v_3 \\ v_4 \\ v_5 \\ v_6 \end{vmatrix} = \begin{vmatrix} s_{11} & s_{12} & s_{13} & s_{14} & s_{15} & s_{16} \\ s_{21} & s_{22} & s_{23} & s_{24} & s_{25} & s_{26} \\ s_{31} & s_{32} & s_{33} & s_{34} & s_{35} & s_{36} \\ s_{41} & s_{42} & s_{43} & s_{44} & s_{45} & s_{46} \\ s_{51} & s_{52} & s_{53} & s_{54} & s_{55} & s_{56} \\ s_{61} & s_{62} & s_{63} & s_{64} & s_{65} & s_{66} \end{vmatrix} \begin{vmatrix} f_1 \\ f_2 \\ f_3 \\ f_4 \\ f_5 \\ f_6 \end{vmatrix} \quad \text{Equation (4)}$$

In equation (4) the matrix terms s11-s66 represent the calibration sensitivity components. The six diagonal terms represent the transducer calibration sensitivities and the 30 off diagonal terms represent the crosstalk terms. Equation (4) may also be represented as $$V = SF \quad \text{Equation (5)}$$

Where V includes the measured outputs and F includes the applied forces and moments. S is the calibration matrix. The calibration procedure determines the components of the calibration matrix S.

Once the calibration matrix is determined and stored in the force platform memory, the force platform is used to measure unknown applied forces by measuring the outputs V and using the inverse of the calibration matrix $S^{-1}$ to determine the applied forces and moments, according to the following equation:

$$F = S^{-1} V \quad \text{Equation (6)}$$

Figure 4:
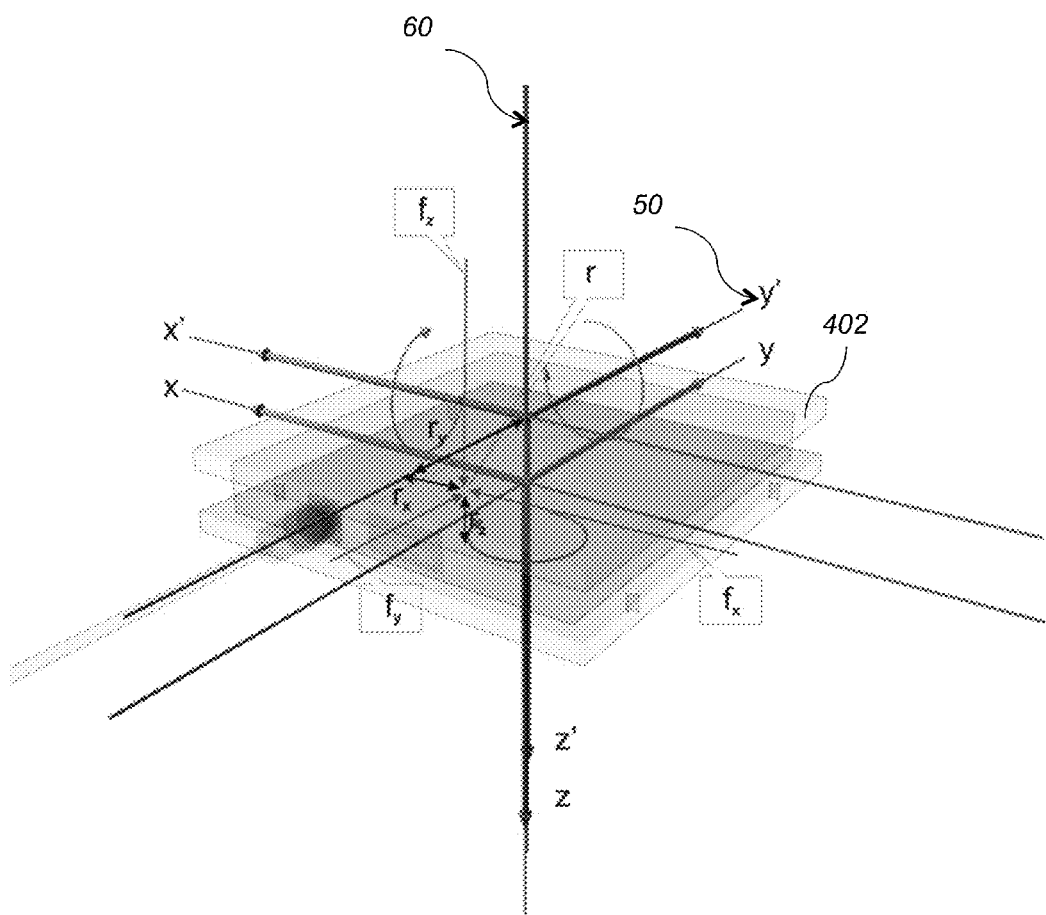
FIG. 4 depicts a physical coordinate system and an electromechanical coordinate system of a force platform used in a prior art calibration procedure.

A typical prior art calibration procedure is described in detail in Appendix A in connection with FIG. 4.

Figure 6A:
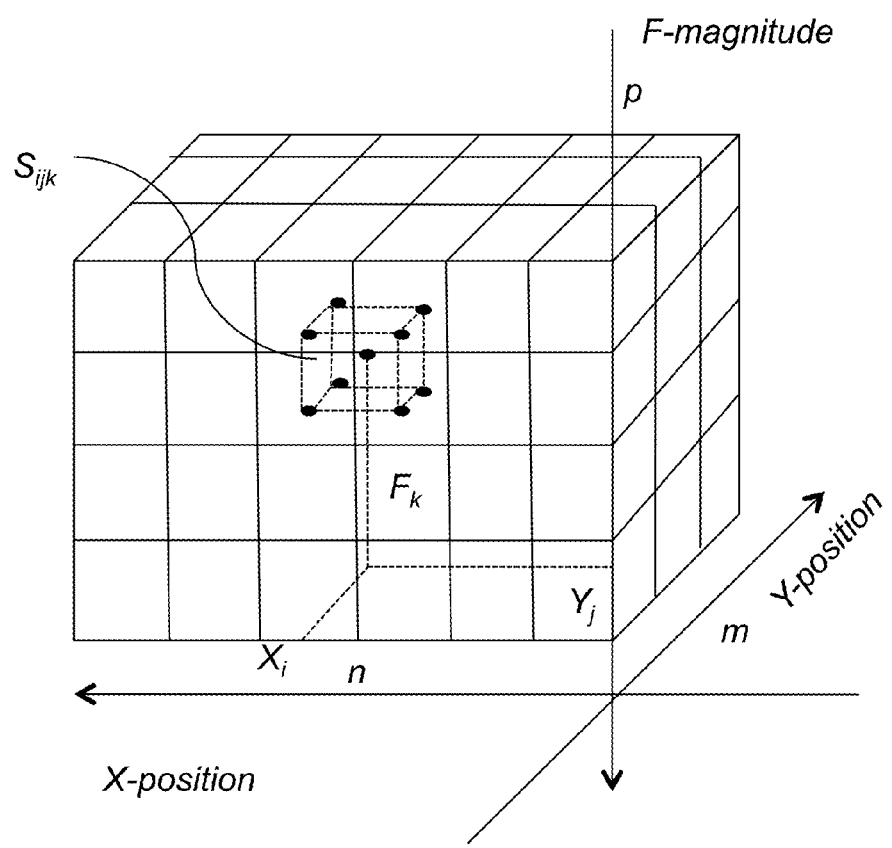
FIG. 6A depicts a 3-D grid used in the calibration process.
Figure 6B:
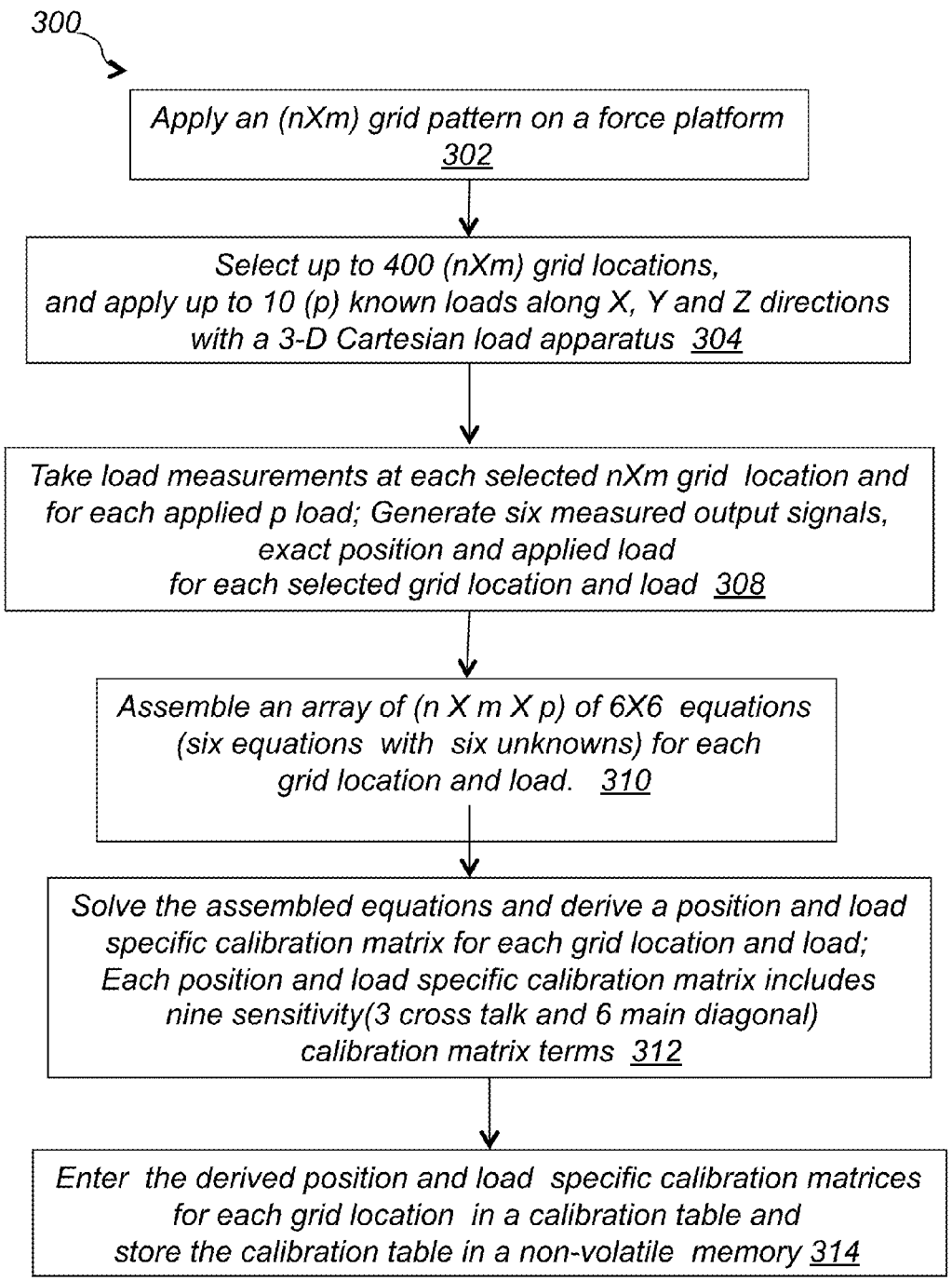
FIG. 6B depicts a flow diagram of the force platform 3-D calibration process according to this invention.
Figure 7:
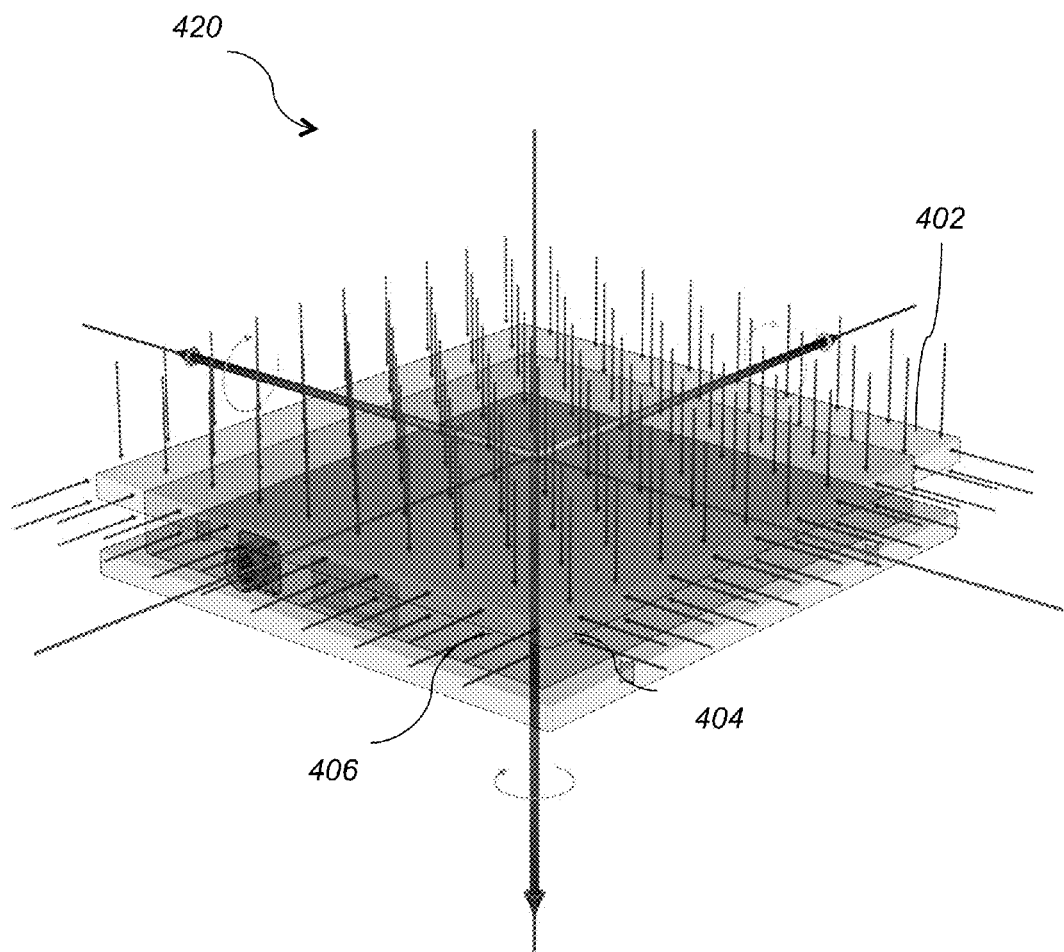
FIG. 7 depicts a 3-D grid applied on a force platform for performing the 3-D calibration procedure of this invention.

Referring to FIG. 6A and FIG. 6B, the improved calibration procedure 300 of the present invention includes the following steps. First, a 3-dimensional (3-D) grid 420 is applied onto the force platform 400 via a computing device, as shown in FIG. 6A (302). The 3-D grid includes n-positions along the X-axis, m-positions along the Y-axis and p-force magnitudes (F-magnitudes) along the Z-axis. In one example, n is in the range of 2-20, m is in the range of 2-20 and p is in the range of 1-10. In the case where n=20, m=20, and p=10, 400 grid positions are defined on the top surface of the force platform 400. At each selected grid position ($X_i$, $Y_j$) ten different loads ($F_k$) are applied from three different directions X, Y and Z, and force platform measurements are taken and recorded. The applied loads include force values from zero to Full Scale Capacity (FSC) at increments of 10%. These measurements generate the above mentioned six output measuring signals (Fx, Fy, Fz, Mx, My, Mz), which are now measured for each grid position and each applied load. In addition to the six output measuring signals, the exact position coordinate of each grid position and the applied load are recorded (308). Next, an array of n×m×p of 6 equations with 6 unknowns (6×6) is assembled for the n×m grid positions and p loads (310). Next, the assembled equations are solved and a position and load specific calibration matrix $S_{ijk}$ is derived for each position and load. Each position and load specific matrix includes nine specific sensitivity (six main diagonal and three crosstalk) terms (312). Next, the derived position and load specific matrices for each grid position and load are entered into a calibration table and the calibration table is stored in a non-volatile memory (314). The non-volatile memory may be incorporated in the force platform or may be an external memory. The system performance is further verified by applying National Institute of Standards and Technology (NIST) traceable dead weights of 50 lbs, 100 lbs and 200 lbs onto the top surface of the force platform (316). Furthermore, secondary characteristics are measured at eight grid locations using a ten point up and ten point down calibration protocol (318). The secondary characteristics include linearity and hysteresis, among others.

Figure 8:
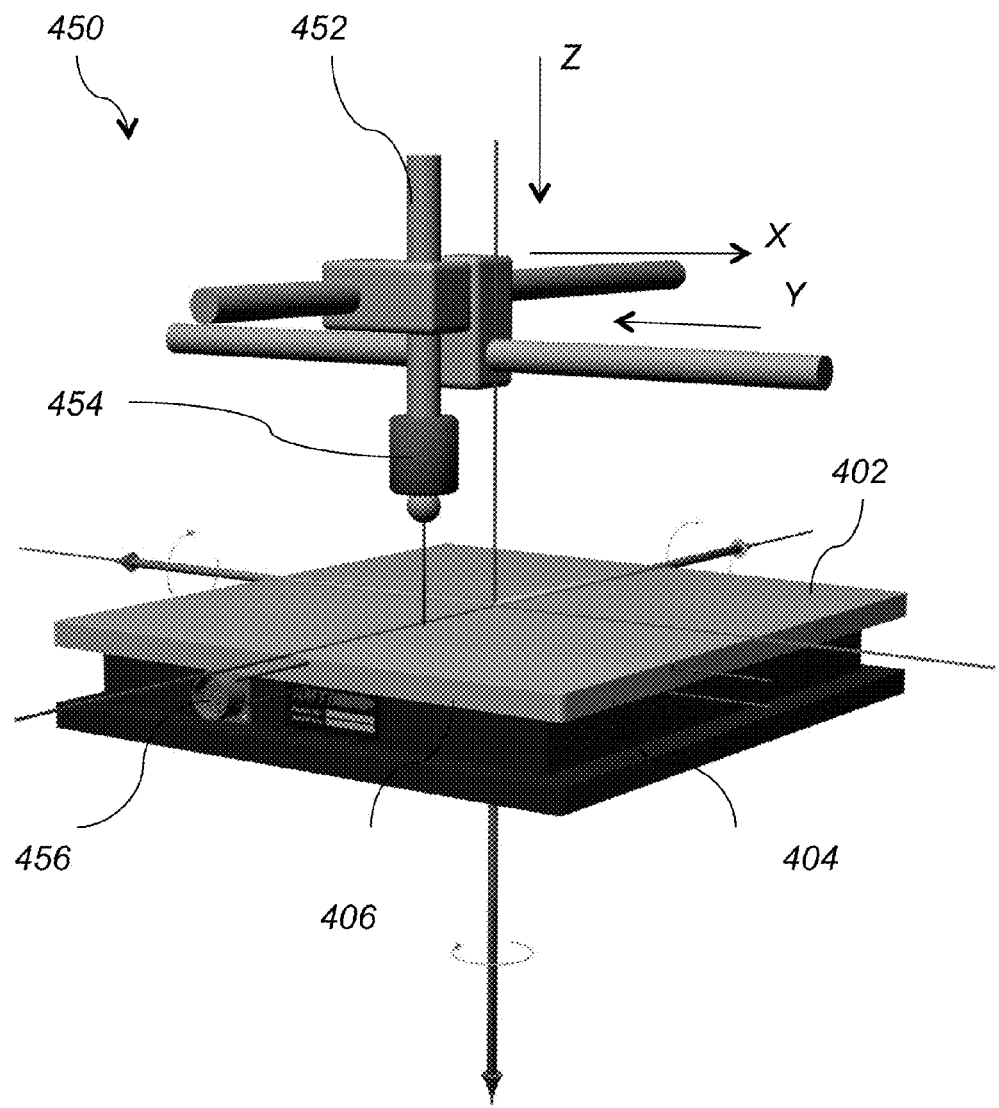
FIG. 8 depicts the 3-D Cartesian load apparatus used in the 3-D calibration procedure of this invention.
Figure 9:
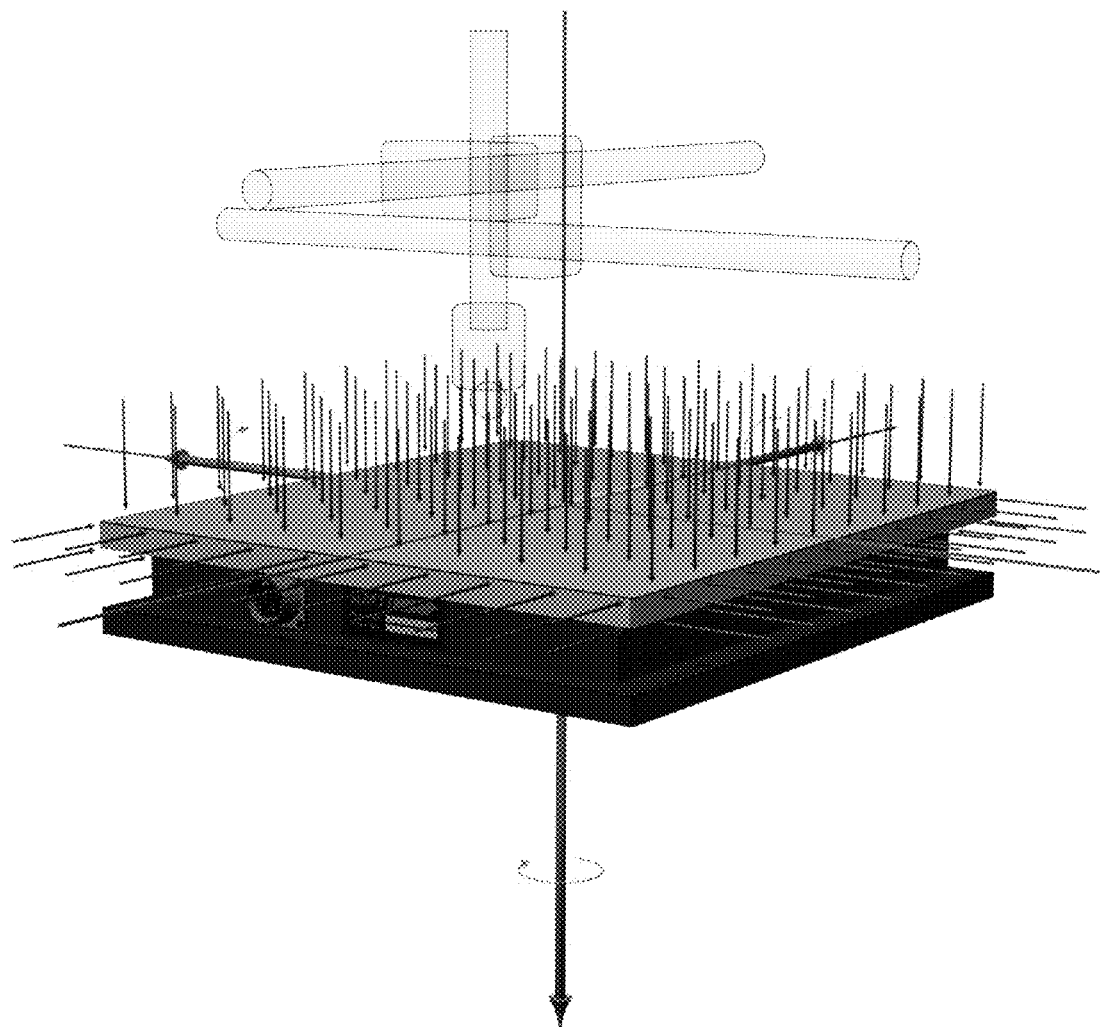
FIG. 9 depicts the 3-D loads applied onto the top surface, the front side surface and the right side surface of the force platform during the 3-D calibration procedure of this invention.

Referring to FIG. 8, the calibration system 450 includes a Cartesian load apparatus 452 having a load applying actuator 454 and at least one transducer 456 measuring loads in X, Y and Z directions. The Cartesian load apparatus 452 is programmed to move from point to point across the top surface 402, the front side surface 406 and the right side surface 404 of the force platform 400. At each programmed point the selected known calibration loads are applied in three different orthogonal load directions (Z, X, Y) and calibration data are measured. Fz loads are applied with a dead weight or an air bearing supported load cell, both of which assure us that there are no shear loads acting on the top surface causing moments Mx or My. The side loads Fx and Fy are applied via the same load cell without the air bearing support. While applying side loads the off axis loads are measured in order to characterize their effect. The three loading conditions permit us to assemble three sets of three equations with three unknowns which can be solved by least squares methods. The Cartesian load apparatus 452 is capable of maintaining positioning accuracy of 0.0001 inches (0.025 mm). In one example, load apparatus 452 locates the weights on a grid spacing of 1 inch (25.4 mm) yielding 300 measurement points on the top surface of the platform. Additional 100 locations are tested on the front and right side surfaces of the platform.

Since we know the three orthogonal loads Fx, Fy, Fz and the point of load application we can determine exactly the moment contribution of each load. Thus we can correct Mx and My for the moment contribution of Fz and then determine the z offset distance. Likewise we can fully determine Mz from Fx and Fy acting at that point. Fz to Mz cross talk can be accurately determined from the Fz loading scenarios. Fx to Mx and Fy to My cross talk is estimated by taking two side load measurements at two different dz's.

Fz loads are applied in a grid pattern extending across the length and width of the plate with the (0,0) point determined to be in the center of the plate. Dead weights are used when possible to assure that there is zero side load. In one example 3 different loads, 50 lbs, 100 lbs and 200 lbs are used. In order to provide a full scale calibration we add at least one additional load point at full scale. Fx and Fy side loads are applied collinear with the top surface grid lines at each grid point. It is somewhat advantageous to apply this load at the edge of the platform top surface, however it is more convenient to apply the load slightly below the top surface. The side load magnitudes are the same as the loads applied on the top surface. The line of action of the side load intersects with multiple load points across the top surface. It is assumed that this side load is applied at each of the nodes of intersection.

The above procedure results in an array of n×m×p of six equations with six unknowns (6×6) for each grid location (n×m) and each load (p). Each equation is informed with three components of force Fx, Fy, Fz and a vector of six transducer outputs. Least squares regression is used to solve for the nine sensitivity (3 cross talk and 6 main diagonal) terms. The procedure also results in two arrays for side loading, an n×2×2 for the front side surface and an m×2×2 array for the right side surface. For the side loading, each equation has two unknowns, including a force to moment cross talk and a dz term. These equations may also be solve using the least squares method.

Figure 10:
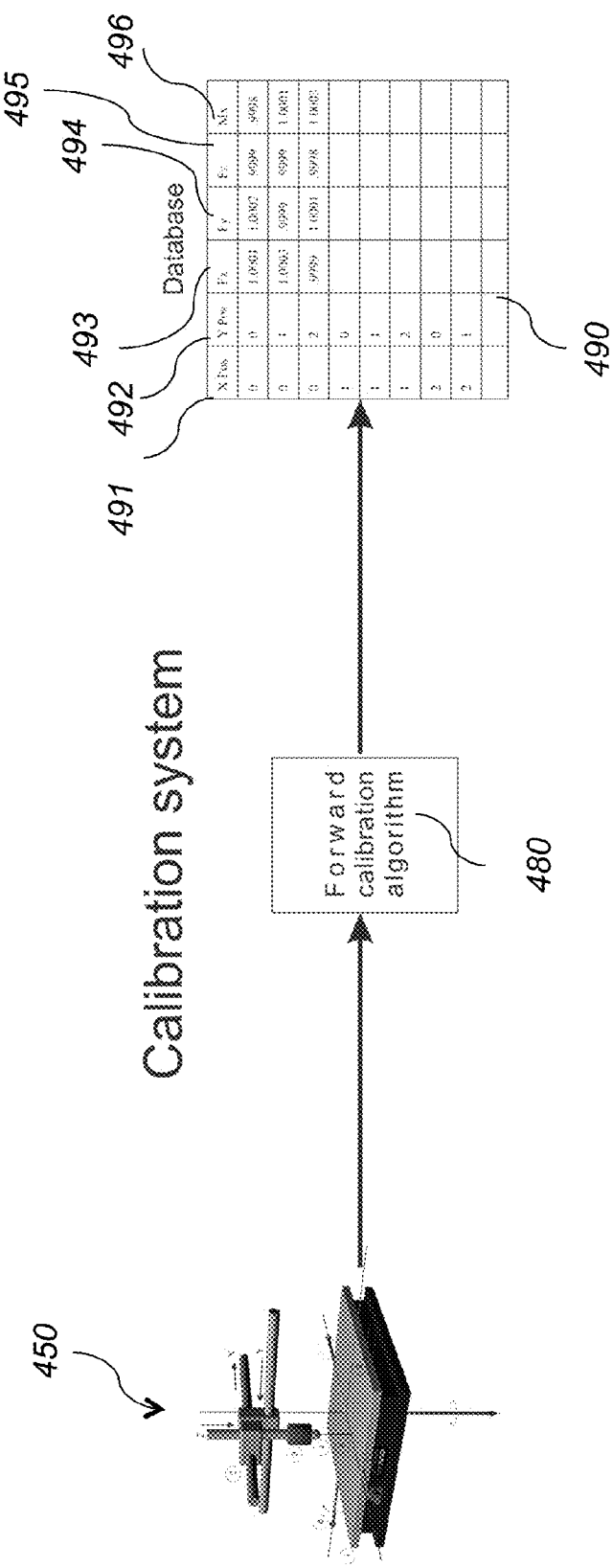
FIG. 10 depicts the force platform 3-D calibration system of this invention.

As was mentioned above, the calibration data at each grid location also include exact grid location, magnitude of the applied load and the six measured force platform output signals. Referring to FIG. 10, forward calibration algorithm 480 is used to derive the sensitivity terms of the calibration matrix for each point and for each applied load. The derived sensitivity matrix terms are stored in a three dimensional table 490 and are indexed by x-y position coordinates 491, 492, and applied load levels (Fx, Fy, Fz and Mx) 493, 494, 495 496, respectively.

Figure 11A:
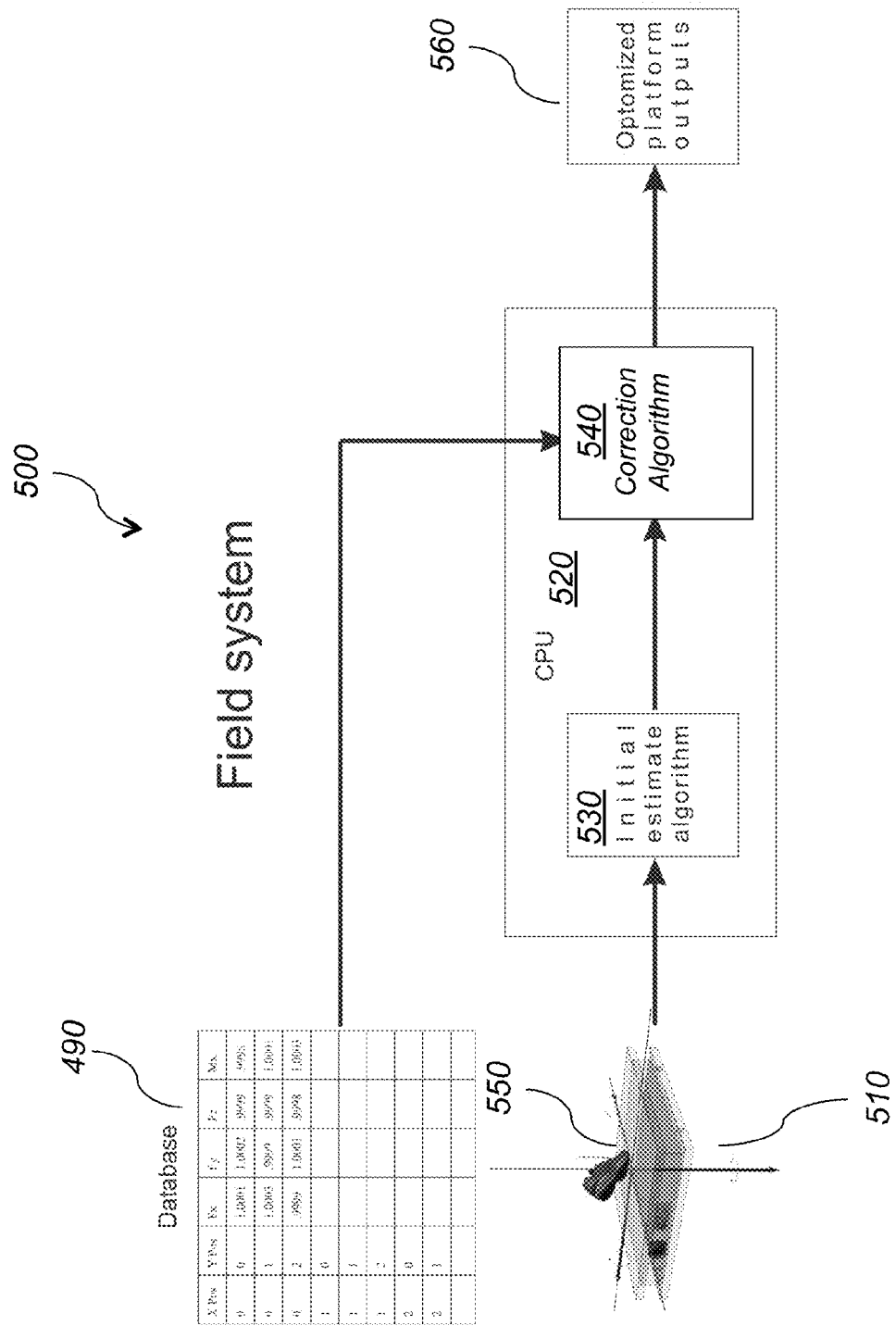
FIG. 11A depicts the force platform measuring system using the 3-D calibrated force platform of this invention.

Referring to FIG. 11A, the field measuring system 500 includes a force platform 510, a computing device 520 including a microprocessor, a digital signal processor or any other central processing unit (CPU), memory configured to store the table 490 with the calibration matrices, an initial estimate algorithm 530 and a correction calibration algorithm 540. Furthermore, global calibration coefficients are also stored in the field system.

Figure 11B:
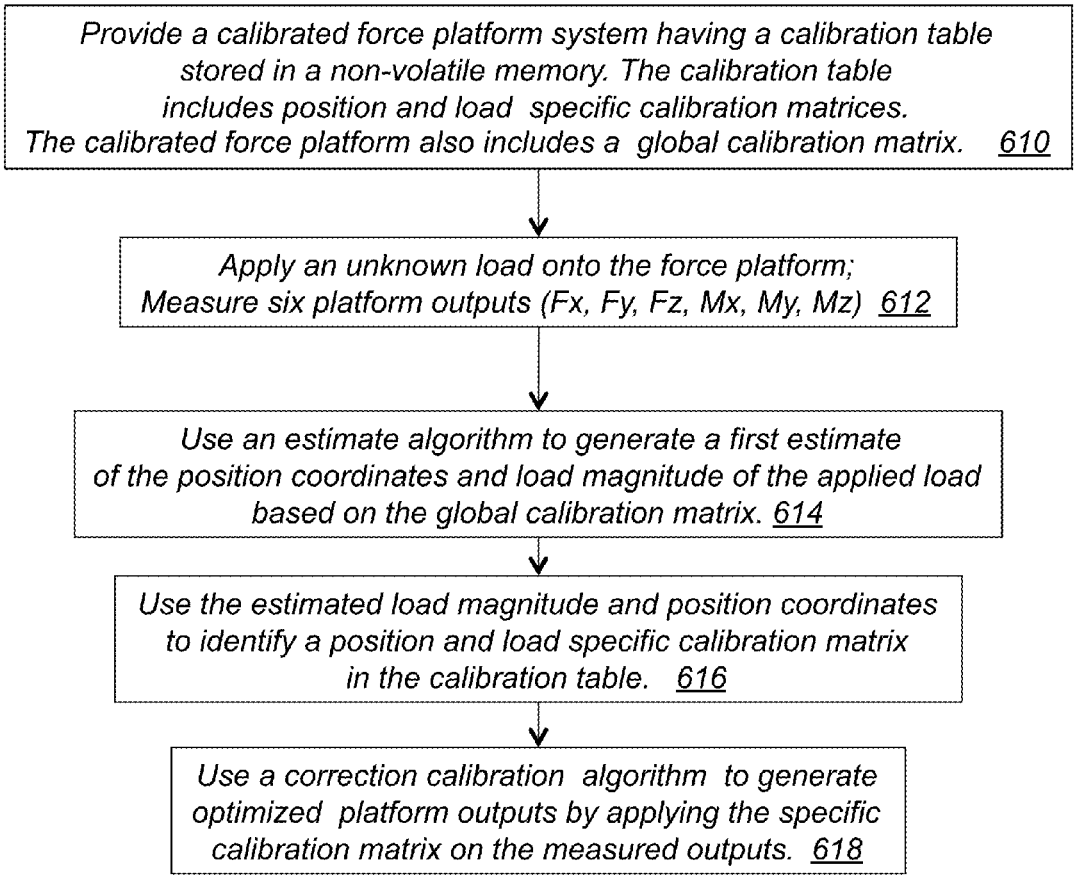
FIG. 11B depicts a flow diagram of the measuring process using the 3-D calibrated force platform of this invention.
Figure 12A:
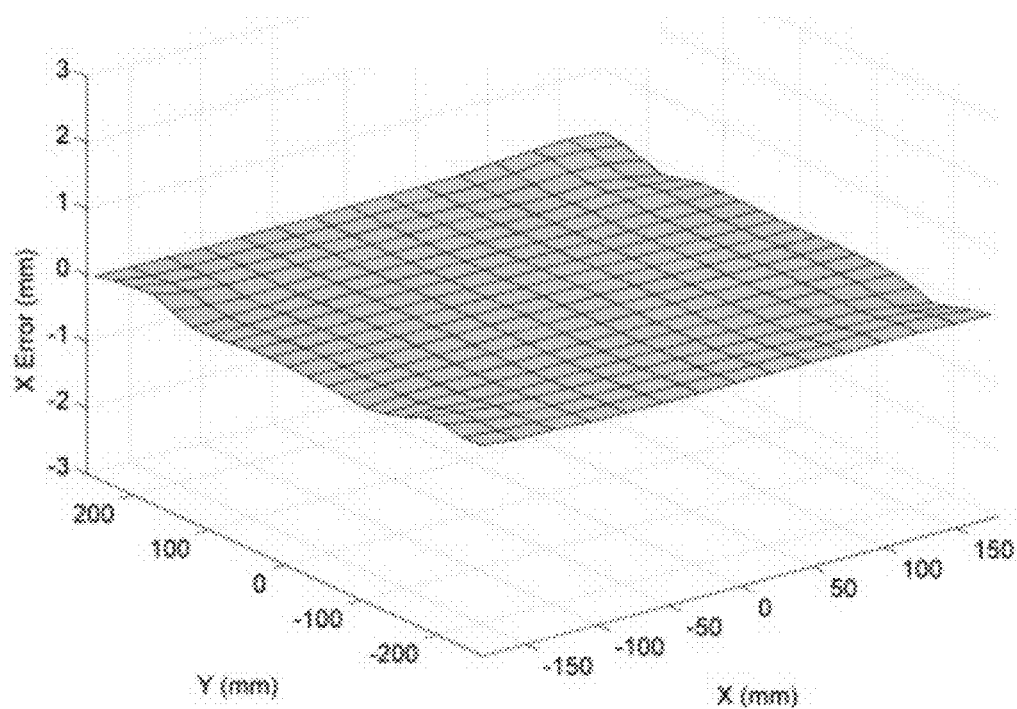
FIG. 12A depicts COPx error distribution generated with the calibration method of this invention.
Figure 12B:
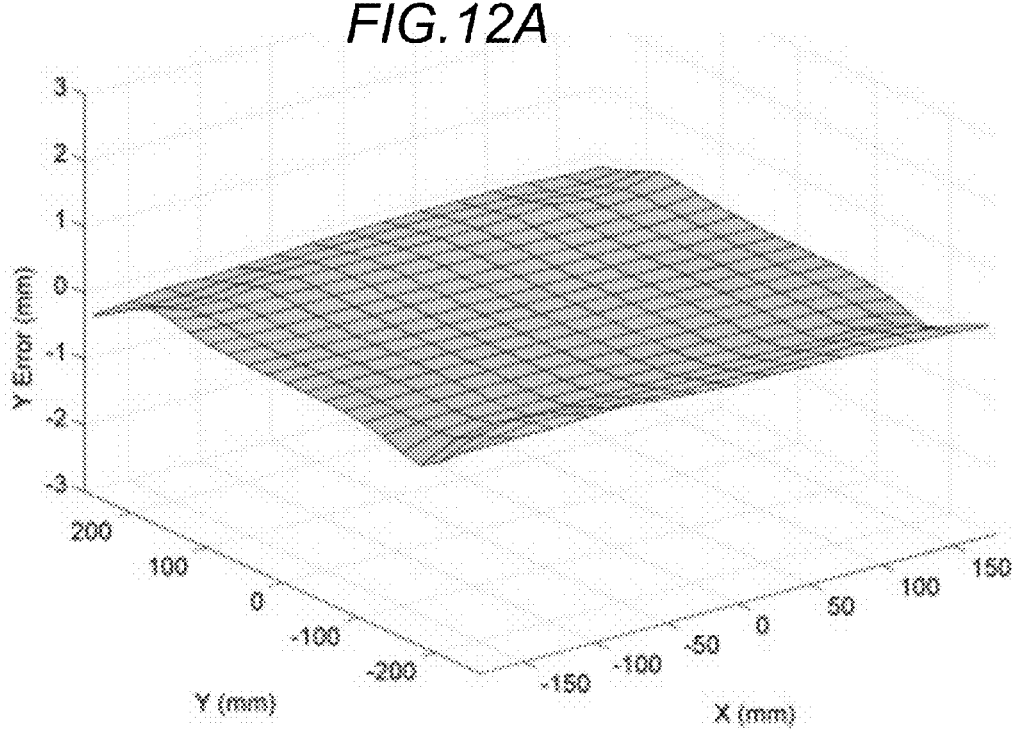
FIG. 12B depicts COPy error distribution generated with the calibration method of this invention.
Figure 12C:
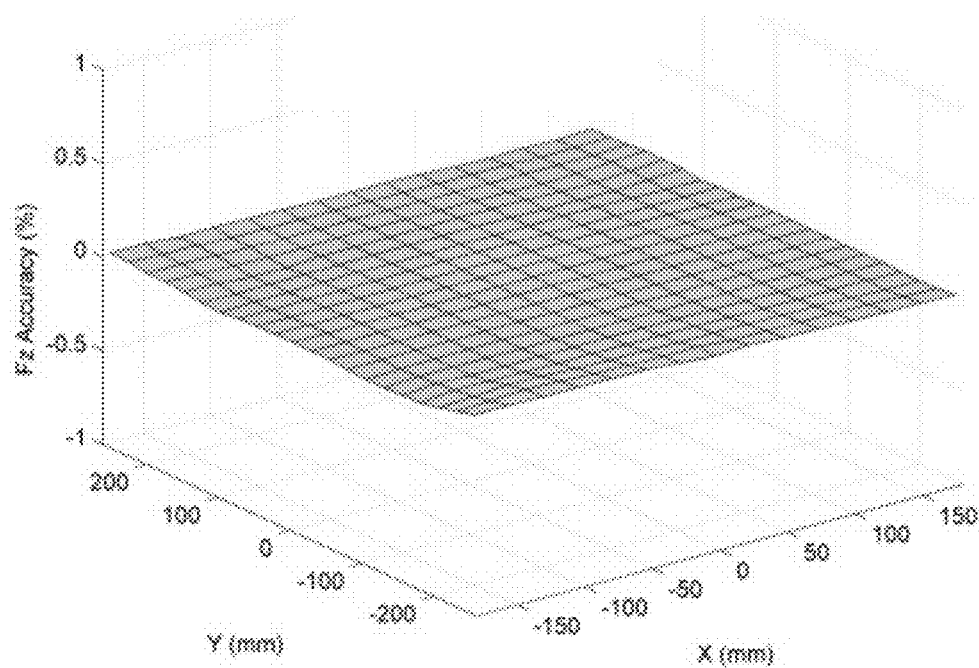
FIG. 12C depicts the Fz error distribution generated with the calibration method of this invention.
Figure 12D:
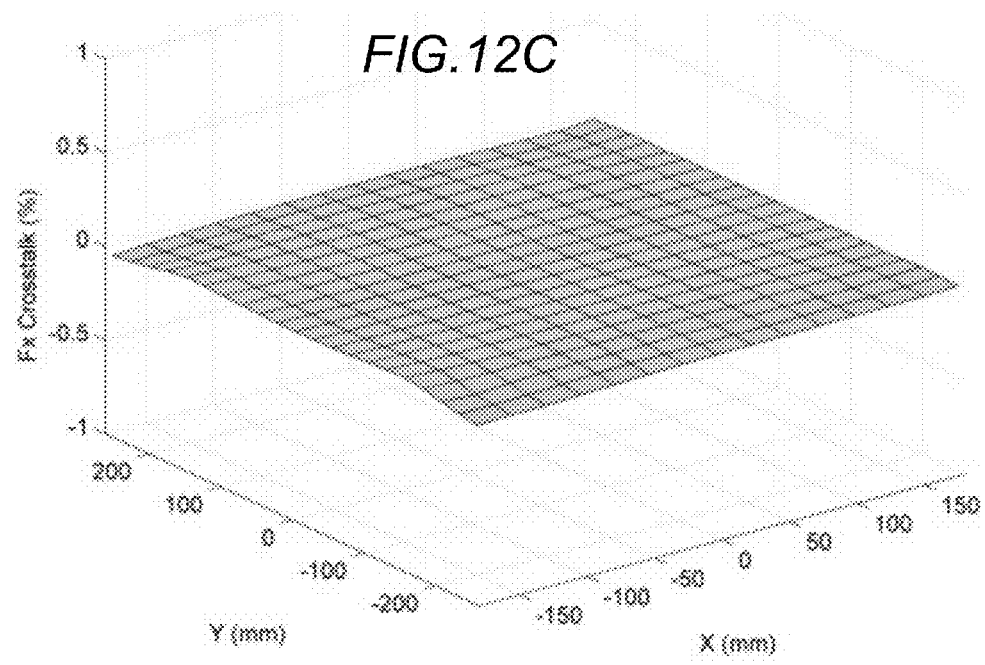
FIG. 12D depicts the Fz to Fx crosstalk error distribution generated with the calibration method of this invention.
Figure 12E:
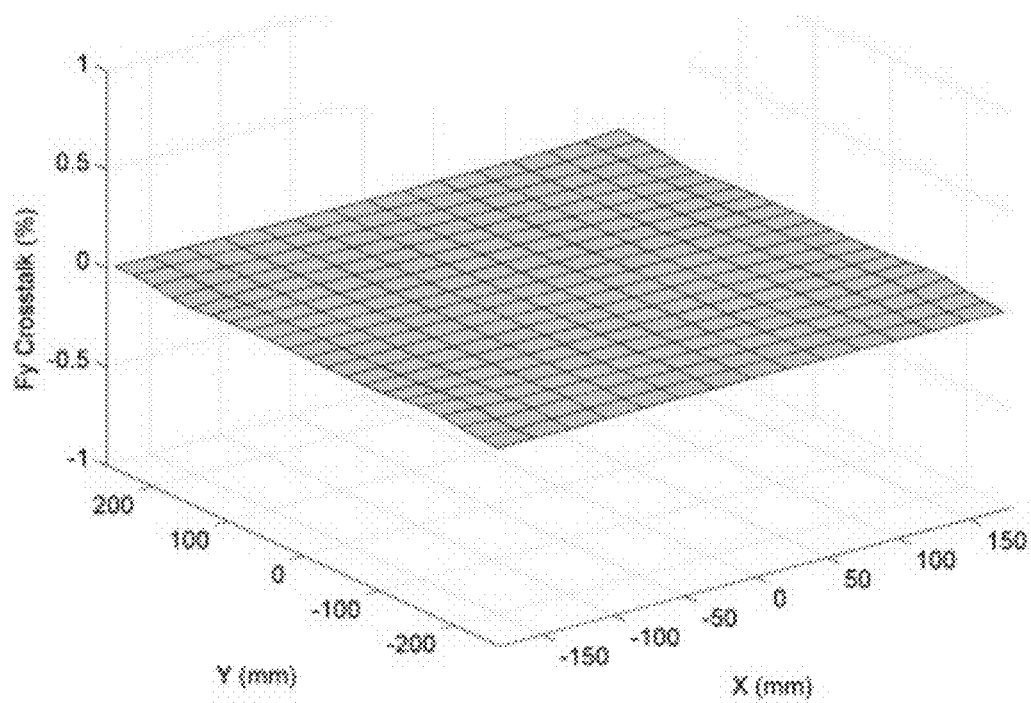
FIG. 12E depicts the Fz to Fy crosstalk error distribution generated with the calibration method of this invention.
Figure 12F:
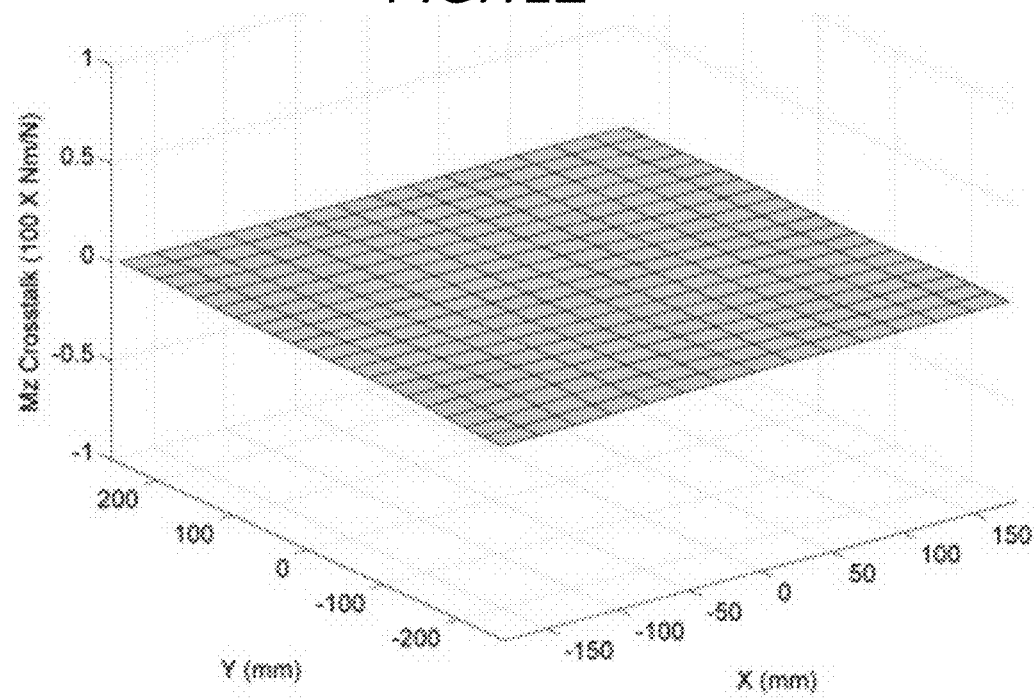
FIG. 12F depicts the Fz to Mz crosstalk error distribution generated with the calibration method of this invention.

Referring to FIG. 11B, in operation, an unknown load 550 is applied on the top surface of the force platform 510 and a set of six measured platform outputs are produced (612). The initial estimate algorithm 530 is used to generate a first estimate of the applied load and position coordinates based on the global calibration coefficients (614). The estimated position coordinates, loads and moments are then used to identify an appropriate position and load specific calibration matrix in table 490 (616). A correction algorithm 540 is then used to apply the identified position and load specific calibration to the measured platform outputs and to produce accurate measures of the applied load 560 (618). This process may be repeated in an iterative way until a preset error level is achieved. One example of the mathematics of the 3-D calibration procedure is described in detail in Appendix B.

Several embodiments of the present invention have been described. Nevertheless, it will be understood that various modifications may be made without departing from the spirit and scope of the invention. Accordingly, other embodiments are within the scope of the following claims.

APPENDIX A

Prior Art Calibration Procedure
Definitions for Calibration Procedure
$^l v_i$=channel output voltage where i corresponds to x, y, or z
$^l m_i$=moment of force around axis x, y, or z as represented by i
$^l T_i$=torque or couple around axis x, y, or z as represented by i
$^l M_i$=total moment (T+m) acting around axis x, y, or z as represented by i
$^l f_i$=force along axis x, y, or z as represented by i
$^l r_i^k$=position of load application relative to an arbitrary physical axis where k is x, y, or z
$^l q_i^k$=position of the zero moment axis relative to the physical axis where k is x, y, or z
$S_{ij}$=Sensitivity where i denotes the input axis while j denotes the output channel The leading superscript l, denotes a specific calibration load point. Multiple load points must be established for each channel calibrated.

Referring to FIG. 4, a physical coordinate system 50 is defined such that its origin lies on the top surface 402 of the force plate 400 with x' and y' axes coplanar with that surface while the z' axis is oriented downward in the center of the physical dimensions of the plate surface. The physical coordinate system 50 is the primed coordinate system (x', y', z') shown in FIG. 4.

Referring again to FIG. 4, an electromechanical coordinate system 60 is defined based on the zero moment axes of the transducer or force plate. The zero moment axes are those axes which result in no moment output when a force acts orthogonally on that axis line. The electromechanical coordinate system 60 is dependent on platform design and fabrication. This coordinate system must be "discovered" by the calibration process. In FIG. 4, this coordinate system is shown by the unprimed axes (x, y, z). The electromechanical coordinate system 60 is positioned relative to the physical coordinate 50 with some offset denoted by $r_x$, $r_y$ and $r_z$. In this analysis these offsets are considered to be the direct distances from the physical axes to the electromechanical axes. As an example the xy plane of the electromechanical coordinate system lies beneath the xy plane of the physical coordinate system (in the positive z direction) so the z offset, $r_z$ is positive.

Each calibration condition involves applying a known load at some point r on the force platform surface. For reference the following moment of force definition is provided.

$$m = r \times f$$

$$m = (r_y f_z - r_z f_y) + (r_z f_x - r_x f_z) + (r_x f_y - r_y f_x)$$

$$m_x = (r_y f_z - r_z f_y)$$

$$m_y = (r_z f_x - r_x f_z)$$

$$m_z = (r_x f_y - r_y f_x)$$

To the first order, neglecting cross talk, the outputs of the transducer are proportional to the inputs as shown in the following equations:

$$v_{fx} \propto f_x$$

$$v_{fy} \propto f_y$$

$$v_{fz} \propto f_z$$

$$V_{mx} \propto T_x + m_x$$

$$v_{my} \propto T_y + m_y$$

$$V_{mz} \propto T_z + m_z$$

The moment channels can be expanded to the sum of pure applied torque and the two moments of force that may arise from the application of orthogonal force components.

$$v_{fx} \propto f_x$$

$$v_{fy} \propto f_y$$

$$v_{fz} \propto f_z$$

$$v_{mx} \propto T_x + (r_y f_z - r_z f_y)$$

$$v_{my} \propto T_y + (r_z f_x - r_x f_z)$$

$$v_{mz} \propto T_z + (r_x f_y - r_y f_x)$$

The above proportional relationships can be rewritten using proportionality constant, S, representing the on axis channel sensitivity.

$$v_{fx} = S_{fxx} f_x$$

$$v_{fy} = S_{fyy} f_y$$

$$v_{fz} = S_{fzz} f_z$$

$$v_{mx} = S_{Mxx}[T_x + (r_y f_z - r_z f_y)]$$

$$v_{my} = S_{Myy}[T_y + (r_z f_x - r_x f_z)]$$

$$v_{mz} = S_{Mzz}[T_z + (r_x f_y - r_y f_x)]$$

Now to develop the calibration concept we consider the force channels, and we neglect the moments for simplicity. Each force output will have some sensitivity (cross talk) to each of the three orthogonal forces.

$$v_{fx} = S_{fxx} f_x + S_{fyx} f_y + S_{zx} f_z$$

$$v_{fy} = S_{fxy} f_x + S_{fyy} f_y + S_{fzy} f_z$$

$$v_{fz} = S_{fxz} f_x + S_{fyz} f_y + S_{fzz} f_z$$

Note that in each force equation there are three unknown sensitivity coefficients (the S terms) while the three input forces (the f terms) are measured or controlled to known values. The outputs (the v terms) are likewise known through the measurement process. Given the three unknown sensitivity terms three linearly independent equations must be established to solve the system of equations.

$$^1v_{fx} = S_{fxx}{}^1 f_x + S_{fyx}{}^1 f_y + S_{fzx}{}^1 f_z$$

$$^2v_{fx} = S_{fxx}{}^2 f_x + S_{fyx}{}^2 f_y + S_{fzx}{}^2 f_z$$

$$^3v_{fx} = S_{fxx}{}^3 f_x + S_{fyx}{}^3 + f_y + S_{fzx}{}^3 f_z$$

The three equations shown above are derived from applying loads in different directions at different load points. The most obvious thing to do is to apply in 1 a pure $f_x$, in two a pure $f_y$ and in three a pure $f_z$. This will result in linearly independent equations exercising the system to develop the three cross talk sensitivities.

The y and z outputs are shown following where the number of load configurations $l_i$, must be at least three in order to solve the set of equations.

$$^l v_{fy} = S^l_{fxy} f_x + S^l_{fyy} f_y + S^l_{fzy} f_z$$

$$\vdots$$

$$^l v_{fz} = S^l_{fxz} f_x + S^l_{fyz} f_y + S^l_{fzz} f_z$$

$$\vdots$$

Moments

We know the point of load application (r) relative to a physical fixed coordinate system 50 for every load point. We do not know position (q) of the electromechanical shear axis or zero moment axis relative to the physical coordinate system. The moment arm relative to the electromechanical zero moment axis is determined as r−q. Thus for each moment of force we wish to consider we introduce a single additional unknown, q, and a known (measured) distance d for each load point.

In the past we have assumed that the electromechanical axes are an orthogonal coordinate system with all axes coincident at a point (the origin) and that a simple axes translation can represent the relationship between the physical and electromechanical coordinate systems. This assumption is considerably in error for our Hall effect platforms which have different z offsets for x and y axes. This assumption may also be in error when considering cross talk effects.

$$v_{mx} = S_{Mxx}[T_x + (r_y f_z - r_z f_y)] + S_{Myx}[T_y + (r_z f_x - r_x f_z)] + S_{Mzx}[T_z + (r_x f_y - r_y f_x)]$$

$$v_{my} = S_{Mxy}[T_x + (r_y f_z - r_z f_y)] + S_{Myy}[T_y + (r_z f_x - r_x f_z)] + S_{Mzy}[T_z + (r_x f_y - r_y f_x)]$$

$$v_{mz} = S_{Mxz}[T_x + (r_y f_z - r_z f_y)] + S_{Myz}[T_y + (r_z f_x - r_x f_z)] + S_{Mzz}[T_z + (r_x f_y - r_y f_x)]$$

Each of the three major terms is multiplied by a single sensitivity value. For instance the first term of the right hand side of the first equation is multiplied by $S_{Mxx}$, which is the principle sensitivity of the $M_x$ output to an $M_x$ input—for complete generality three different sensitivity terms should be determined, one for each loading condition represented within the brackets.

The first term of the right hand side of the first equation is expanded as follows:

$$v_{mx} = S_{Mxx}[T_x + (r_y f_z - r_z f_y)]$$

$$v_{mx} = S_{Mxx} T_x + S_{Mxx} r_y f_z - S_{Mxx} r_z f_y$$

A completely general solution to the calibration problem would take the following form which does not assume that the sensitivity to pure torque and the two different moment of force loading configurations are the same. This generalization is shown in the following equation.

$$v_{mx} S_{MxTx} T_x + S_{Mxm1x} r_y f_z + S_{Mxm2x} r_z f_y$$

This generalized solution would result in nine sensitivity terms for the moments and three sensitivity terms for the forces, or twelve independent terms for each moment channel to be determined.

It is assumed that the effects of the different loading conditions are negligible, and that a single sensitivity term may be applied to each of the three moment loading conditions representing the principle terms as well as the cross talk terms. It is further assumed that the pure torque, T, loading condition may be neglected and hence pure torques are not applied to the transducers during calibration. These assumptions reduce the set of moment equations to the following:

$$v_{mx} = S_{Mxx}[(r_y f_z - r_z f_y)] + S_{Mxy}[(r_z f_x - r_x f_z)] + S_{Mxz}[(r_x f_y - r_y f_x)]$$

$$v_{my} = S_{Mxy}[(r_y f_z - r_z f_y)] + S_{Myy}[(r_z f_x - r_x f_z)] + S_{Mzy}[(r_x f_y - r_y f_x)]$$

$$v_{mz} = S_{Mxy}[(r_y f_z - r_z f_y)] + S_{Myz}[(r_z f_x - r_x f_z)] + S_{Mzz}[(r_x f_y - r_y f_x)]$$

Up to this point we have been assuming that the moment channel outputs are proportional to the applied loads multiplied by the distance r from some physical coordinate system. In fact the outputs are proportional to the product of the applied force and the distance to an axis representing the zero moment axis for a given orientation of applied load. In the following equations a distance q is introduced which is the distance from the zero moment axis to the physical coordinate system axis.

$$v_{mx} = S_{Mxx}[((r_y - q_y) f_z - (r_z - q_z) f_y)] + S_{Myx}[((r_z - q_z) f_x - (r_x - q_x) f_z)] + S_{Mzx}[((r_x - q_x) f_y - (r_y - q_y) f_x)]$$

$$v_{my} = S_{Myy}[((r_y - q_y) f_z - (r_z - q_z) f_y)] + S_{Myy}[((r_z - q_z) f_x - (r_x - q_x) f_z)] + S_{Mzy}[((r_x - q_x) f_y - (r_y - q_y) f_x)]$$

$$v_{mz} = S_{Mxz}[((r_y - q_y) f_z - (r_z - q_z) f_y)] + S_{Myz}[((r_z - q_z) f_x - (r_x - q_x) f_z)] + S_{Mzz}[((r_x - q_x) f_y - (r_y - q_y) f_x)]$$

Consider two sets of data taken under different conditions, for each of the moment output channels $v_{mx}$, $V_{my}$, and $V_{mz}$, designated by the leading superscript a for one condition and the leading superscript b for the second condition. Mechanical conditions are chosen for a and b such that the main diagonal components of the system of equations are subjected to a nearly full range difference. As an example for $v_{mx}$ the conditions relating to $S_{Mxx}$ are modified while all other terms are held constant. Ideally, diagonal forces are controlled to be zero or near zero. The most relevant loading pattern for a given moment channel is chosen as the pattern to exercise. In the case of $v_{mx}$, $r_y$ is chosen to be modified for conditions a and b-$r_y$ should be changed from its minimum value to its maximum value to develop the most accurate representation of the channel sensitivity.

$$^a v_{mx} = S_{Mmx}[((^a r_y - q_y)^a f_z - (^a r_z - q_z)^a f_y)] + S_{Myz}[((^a r_z - q_z)^a f_x - (^a r_x - q_x)^a f_z)] + S_{Myx}[((^a r_x - q_x)^a f_y - (^a r_y - q_y)^a f_x)]$$

$$^a v_{my} = S_{Mxy}[((^a r_y - q_y)^a f_z - (^a r_z - q_z)^a f_y)] + S_{Myy}[((^a r_z - q_z)^a f_z - (^a r_x - q_x)^a f_z)] + S_{Mzy}[((^a r_x - q_x)^a f_y - (^a r_y - q_y)^a f_x)]$$

$$^a v_{mz} = S_{Mxz}[((^a r_y - q_y)^a f_z - (_a r_z - q_z) f_y)] + S_{Myz}[((^a r_z - q_z)_a f_z - (^a r_x - q_x)^a f_z)] + S_{Mzz}[((^a r_x - q_x)^a f_y - (^a r_y - q_y)^a f_x)]$$

$$^b v_{mx} = S_{Mxx}[((^b r_y - q_y)^b f_z - (^b r_z - q_z)^b f_y)] + S_{Myx}[((^b r_z - q_z)^b f_x - (^b r_x - q_x)^b f_z)] + S_{Mzx}[((^b r_x - q_x)^b f_y - (^b r_y - q_y)^b f_x)]$$

$$^b v_{my} = S_{Mxy}[((^b r_y - q_y)^b f_z - (^b r_z - q_z)^b f_y)] + S_{Myy}[((^b r_z - q_z)^b f_x - (^b r_x - q_x)^b f_z)] + S_{Mzy}[((^b r_z - q_z) f_y - (^b r_y - q_y)^b f_x)]$$

$$^b v_{mz} = S_{Myz}[((^b r_y - q_y)^b f_z - (^b r_z - q_z)^b f_y)] + S_{Myz}[((^b r_z - q_z)^b f_x - (^b r_x - q_x)^b f_z)] + S_{Mzz}[((^b r_x - q_x)^b f_y - (^b r_y - q_y)^b f_x)]$$

The difference between the a conditions and b conditions are determined by subtracting the two conditions. In the following $\Delta v_{mx} = {^a}v_{mx} - {^b}v_{mx}$ etc. It is important to note that in order for this difference to be true the forces must be constant from condition a to condition b, in other words: $f_x = {^a}f_x = {^b}f_x$, $f_y = {^a}f_y = {^b}f_y$, and $f_z = {^a}f_z = {^b}f_z$.

Generalized Calibration Approach

The overall approach to the calibration is as follows:

1) Develop the moment to moment sensitivities using the difference equation approach. This requires three independent difference equations or six independent equations for each moment output—a total of 18 equations.
2) Use the original moment equations to solve for the axis offsets $q_x$, $q_y$, and $q_z$. A generalized approach would yield nine such offsets. Practically we seek one for each of $q_x$, $q_y$ and perhaps two for $q_z$.
3) Develop the force output sensitivities using the combined six term output equations. This involves six equations for each force output term or a total of 18 equations.
4) Redevelop the moment output terms using the axis offsets. This involves six equations for each moment output term or a total of 18 equations.

1) Calculation of Sensitivities for Moment Terms

The first task is to determine the moment sensitivities. As discussed above difference equations are developed for each of the moment channels. The difference equations essentially eliminate the unknown offset terms (i.e., the position of the electro mechanical axes relative to the physical axes) from the equation set permitting a solution by least squares to determine the moment coefficients. These equations are developed following.

$$^a v_{mx} = S_{Mxx}[(^a r_y - q_y)^a f_z (^a r_z - q_z)^a f_y)] + S_{Myx}[((^a r_z - q_z)^a f_x - (^a r_x - q_x)^a f_z)] + S_{Mzx}[((^a r_x - q_x)^a f_y - (^a r_y - q_y)^a f_x)]$$

$$^b v_{mx} = S_{Mxx}[((^b r_y - q_y)^b f_z - (^b r_z - q_z)^b f_y)] + S_{Myx}[((^b r_z - q_z)^b f_x - (^b r_x - q_x)^b f_z)] + S_{Mzx}[((^b r_x - q_x)^b f_y - (^b r_y - q_y)^b f_x)]$$

$$\overline{\Delta v_{mx} = S_{Mxx}[((^a r_y - {^b}r_y) f_z - (^a r_z - {^b}r_z) f_y)] + S_{Myx}[((^a r_z - {^b}r_z) f_x - (^a r_x - {^b}r_x) f_z)] + S_{Mzx}[((^a r_x - {^b}r_x) f_y - (^a r_y - {^b}r_y) f_x)]}$$

$$^a v_{my} = S_{Mxy}[((^a r_y - q_y)^a f_z - (^a r_z - q_z)^a f_y)] + S_{Myy}[((^a r_z - q_z)^a f_x - (^a r_x - q_x)^a f_z)] + S_{Mzy}[((^a r_x - q_x)^a f_y - (^a r_y - q_y)^a f_x)]$$

$$^b v_{my} = S_{Mxy}[((^b r_y - q_y)^b f_z - (^b r_z - q_z)^b f_y)] + S_{Myy}[((^b r_z - q_z)^b f_x - (^b r_x - q_x)^b f_z)] + S_{Mzy}[((^b r_x - q_x)^b f_y - (^b r_y - q_y)^b f_x)]$$

$$\overline{\Delta v_{my} = S_{Mxy}[((^a r_y - {^b}r_y) f_z - (^a r_z - {^b}r_z) f_y)] + S_{Myy}[((^a r_z - {^b}r_z) f_x - (^a r_x - {^b}r_x) f_z)] + S_{Mzy}[((^a r_x - {^b}r_x) f_y - (^a r_y - {^b}r_y) f_x)]}$$

-continued $$^a v_{mz} = S_{Mxz}[((^a r_y - q_y)^a f_z - (^a r_z - q_z)^a f_y)] + S_{Myz}[((^a r_z - q_z)^a f_x - (^a r_x - q_x)^a f_z)] + S_{Mzz}[((^a r_x - q_x)^a f_y - (^a r_y - q_y)^a f_x)]$$

$$^b v_{mz} = S_{Mxz}[((^b r_y - q_y)^b f_z - (^b r_z - q_z)^b f_y)] + S_{Myz}[((^b r_z - q_z)^b f_x - (^b r_x - q_x)^b f_z)] + S_{Mzz}[((^b r_x - q_x)^b f_y - (^b r_y - q_y)^b f_x)]$$

$$\Delta v_{mz} = S_{Mxz}[((^a r_y - ^b r_y)f_z - (^a r_z - ^b r_z)f_y)] + S_{Myz}[((^a r_z - ^b r_z)f_x - (^a r_x - ^b r_x)f_z)] + S_{Mzz}[((^a r_x - ^b r_x)f_y - (^a r_y - ^b r_y)f_x)]$$

In order to develop the main diagonal sensitivity and the two of diagonal cross talk sensitivities for each moment channel three sets of these difference equations must be established for each moment channel (a total of 6 equations for each of three channels or 18 equations).

Thus three difference equations can be used to determine the moment sensitivities. The mechanical requirement is that the loads be equal for each of the load points—this requirement allows the q terms to be reduced to zero in the difference. The terms $q_x$ and $q_y$ are generally quite small so the error expected from a small difference in loading conditions will be negligible. The $q_z$ term is significant therefore it is necessary to equate $f_x$ and $f_y$ under the two load conditions rather carefully. These forces should be either controlled to zero or caused to be near zero with adequate fixturing.

$$^1\Delta v_{mx} = S_{Mxx}{}^1[((^a r_y - ^b r_y)f_z - (^a r_z - ^b r_z)f_y)] + S_{Myx}{}^1[((_a r_z - ^b r_z)f_x - (^a r_x - ^b r_x)f_z)] + S_{Mzx}{}^1[((^a r_x - ^b r_x)f_y - (^a r_y - ^b r_y)f_x)]$$

$$^2\Delta v_{mx} = S_{Mxx}{}^2[((^a r_y - ^b r_y)f_z - (^a r_x - ^b r_x)f_y)] + S_{Myx}{}^2[((^a r_z - ^b r_z)f_x - (^a r_x - ^b r_x)f_z)] + S_{Mzx}{}^2[((^a r_x - ^b r_x)f_y - (^a r_y - ^b r_y)f_x)]$$

$$^3\Delta v_{mx} = S_{Mzx}{}^3[((^a r_y - ^b r_y)f_z - (_a r_z - ^b r_z)f_y)] S_{Myx}{}^3[+((^a r_z - ^b r_z)f_x - (^a r_x - ^b r_x)f_z)] + S_{Mzx}{}^3[((^a r_z - ^b r_z)f_y - (^a r_y - ^b r_y)f_x)]$$

$$^1\Delta v_{my} = S_{Mxy}{}^1[((^a r_y - ^b r_y)f_z - (^a r_z - ^b r_z)f_y)] + S_{Myy}{}^1[((^a r_z - ^b r_z)f_x - (^a r_x - ^b r_x)f_z)] + S_{Mzy}{}^1[((^a r_x - ^b r_x)f_y - (^a r_y - ^b r_y)f_x)]$$

$$^2\Delta v_{my} = S_{Mxy}{}^2[((^a r_y - ^b r_y)f_z - (^a r_z - ^b r_z)f_y)] + S_{Myy}{}^2[((^a r_z - ^b r_z)f_x - (^a r_x - ^b r_x)f_z)] + S_{Mzy}{}^2[((^a r_x - ^b r_x)f_y - (^a r_y - ^b r_y)f_x)]$$

$$^3\Delta v_{my} = S_{Mxy}{}^3[((^a r_y - ^b r_y)f_z - (^a r_z - ^b r_z)f_y)] + S_{Myy}{}^3[((^a r_z - ^b r_z)f_x - (^a r_x - ^b r_x)f_z)] + S_{Mzy}{}^3[((^a r_y - ^b r_y)f_y - (^a r_y - ^b r_y)f_x)]$$

$$^1\Delta v_{mz} = S_{Mxz}{}^1[((^a r_y - ^b r_y)f_z - (^a r_z - ^b r_z)f_y)] + S_{Myz}{}^1[((^a r_z - ^b r_z)f_x - (^a r_x - ^b r_x)f_z)] + S_{Mzz}{}^1[((^a r_x - ^b r_x)f_y - (^a r_y - ^b r_y)f_x)]$$

$$^2\Delta v_{mz} = S_{Mxz}{}^2[((^a r_y - ^b r_y)f_z - (^a r_z - ^b r_z)f_y)] + S_{Myz}{}^2[((^a r_z - ^b r_z)f_x - (^a r_x - ^b r_x)f_z)] + S_{Mzz}{}^2[((^a r_x - ^b r_x)f_y - (^a r_y - ^b r_y)f_x)]$$

$$^3\Delta v_{mz} = S_{Mxz}{}^3[((^a r_y - ^b r_y)f_z - (^a r_z - ^b r_z)f_y)] + S_{Myz}{}^3[((^a r_z - ^b r_z)f_x - (^a r_x - ^b r_x)f_z)] + S_{Mzz}{}^3[((^a r^2 - ^b r_z)f_y + (^a r_y - ^b r_y)f_x)]$$

Each of the set of three difference equations is generated from a different set of loading conditions. These conditions are devised to provide a linearly independent set of equations. The main diagonal term, $S_{Mxx}$ is developed by maximizing the difference between $^1 r_y$ and $^2 r_y$ while applying an $f_z$ load. In this case $r_x$, $r_z$ are held constant while $f_x$ and $f_y$ are minimized. The second load condition represented by the difference pair $^3 v_{mx} - ^4 v_{mx}$ develops the cross talk term $S_{Myx}$. The best approach for this term will be to apply an $f_z$ force at different x positions while holding $r_z$ and $f_y$ constant.

The required 18 equations are derived from six different load configurations highlighted by the red font in the above equations.

2) Calculation of Offset Terms

The offsets $q_x$, $q_y$, and $q_z$ are determined from the raw moment equations by substituting in the moment sensitivities calculated with the difference approach described above.

For reference the moment equations are restated following:

$$v_{mx} = S_{Mxx}[((r_y - q_y)f_z - (r_z - q_z)f_y)] + S_{Myx}[((r_z - q_z)f_x - (r_x - q_x)f_z)] + S_{Mzx}[((r_x - q_x)f_y - (r_y - q_y)f_x)]$$

$$v_{my} = S_{Mxy}[((r_y - q_y)f_z - (r_z - q_z)f_y)] + S_{Myy}[((r_z - q_z)f_x - (r_x - q_x)f_z)] + S_{Mzy}[((r_x - q_x)f_y - (r_y - q_y)f_x)]$$

$$v_{mz} = S_{Mxz}[((r_y - q_y)f_z - (r_z - q_z)f_y)] + S_{Myz}[((r_z - q_z)f_x - (r_x - q_x)f_z)] + S_{Mzz}[((r_x - q_x)f_y - (r_y - q_y)f_x)]$$

All of the terms are known except the offsets $q_x$, $q_y$, and $q_z$. These equations are expanded and known terms are collected and moved to the left side of the equations as follows:

$$^1 v_{mx} - S_{Mxx}[(r_y f_z - r_z f_y)] + S_{Myx}[(r_z f_x - r_x f_z)] + S_{Mzx}[(r_x f_y - r_y f_x)] = S_{Mxx}[(q_z f_y - q_y f_z)] + S_{Myx}[(q_x f_z - q_z f_x)] + S_{Mzx}[(q_y f_x - q_x f_y)]$$

$$^2 v_{my} - S_{Mxy}[(r_y f_z - r_z f_y)] + S_{Myy}[(r_z f_x - r_x f_z)] + S_{Mzy}[(r_x f_y - r_y f_x)] = S_{Mxy}[(q_z f_y - q_y f_z)] + S_{Myy}[(q_x f_z - q_z f_x)] + S_{Mzy}[(q_y f_x - q_x f_y)]$$

$$^3 v_{mz} - S_{Mxz}[(r_y f_z - r_z f_y)] + S_{Myz}[(r_z f_x - r_x f_z)] + S_{Mzz}[(r_x f_y - r_y f_x)] = S_{Mxz}[(q_z f_y - q_y f)] + S_{Myz}[(q_x f_z - q_z f_x)] + S_{Mzz}[(q_y f_x - q_x f_y)]$$

On collecting like terms on the right hand side we have the following three equations in three unknowns, $q_x$, $q_y$ and $q_z$ the electromechanical axes offsets.

$$^1 v_{mx} - S_{Mxx}[(r_y f_z - r_z f_y)] + S_{Myx}[(r_z f_x - r_x f_z)] + S_{Mzx}[(r_x f_y - r_y f_x)] = [S_{Myx} f_z - S_{Mzx} f_y]q_x + [S_{Mzx} f_x - S_{Mxx} f_z]q_y + [S_{Mxx} f_y - S_{Myx} f_x]q_z$$

$$^2 v_{my} - S_{Mxy}[(r_y f_z - r_z f_y)] + S_{Myy}[(r_z f_x - r_x f_z)] + S_{Mzy}[(r_x f_y - r_y f_x)] = [S_{Myy} f_z - S_{Mzy} f_y]q_x + [S_{Mzy} f_x - S_{Mxy} f_z]q_y + [S_{Mxy} f_y - S_{Myy} f_x]q_z$$

$$^3 v_{mz} - S_{Mxz}[(r_y f_z - r_z f_y)] + S_{Myz}[(r_z f_x - r_x f_z)] + S_{Mzz}[(r_x f_y - r_y f_x)] = [S_{Myz} f_z - S_{Mzz} f_y]q_x + [S_{Mzz} f_x - S_{Mxz} f]q_y + [S_{Mxz} f_y - S_{Myz} f_x]q_z$$

It should be noted that the $q_z$ terms have been aggregated, however, if it were desirable to develop $q_z$ terms for $m_x$ and $m_y$ independently these terms could be maintained independently.

$$v_{mx} = d^{\alpha x}{}_y S_{Mxx} f_z - d^{\alpha x}{}_z S_{Mxx} f_y + d^{\beta y}{}_z S_{Myx} f_x - d^{\beta y}{}_x S_{Myx} f_z + d^{\gamma z}{}_x S_{Mzx} f_y - d^{\gamma z}{}_y S_{Mzx} f_x$$

$$v_{my} = d^{\alpha x}{}_y S_{Mxy} f_z - d^{\alpha x}{}_z S_{Mxy} f_y + d^{\beta y}{}_z S_{Myy} f_x - d^{\beta y}{}_x S_{Myy} f_z + d^{\gamma z}{}_x S_{Mzy} f_y - d^{\gamma z}{}_y S_{Mzy} f_x$$

$$v_{mz} = d^{\alpha x}{}_y S_{Mxz} f_z - d^{\alpha x}{}_z S_{Mxz} f_y + d^{\beta y}{}_z S_{Myz} f_x - d^{\beta y}{}_x S_{Myz} f_z + d^{\gamma z}{}_x S_{Mzz} f_y - d^{\gamma z}{}_y S_{Mzz} f_x$$

3) Equations for Calculation of Force Sensitivity Terms

In steps 3 and 4 the d terms are now taken to be the r-q terms developed above. For example $d_x = r_x - q_x$, $d_y = r_y - q_y$, and $d_z = r_z - q_z$.

$$v_{fx} = S_{fxfx} f_x + S_{fyfx} f_y + S_{fzfx} f_z + S_{Mxfx}[d_y f_z - d_z f_y] + S_{Myfx}[d_z f_x - d_x f_z] + S_{Mzfx}[d_x f_y - d_y f_x]$$

$v_{fy}=S_{fxfy}f_x+S_{fyfy}f_y+S_{fzfy}f_z+S_{Mxfx}[d_yf_z-d_zf_y]+S_{Myfy}[d_zf_x-d_xf_z]+S_{Mzfy}[d_xf_y-d_yf_x]$ $v_{fz}=S_{fxfz}f_x+S_{fyfz}f_y+S_{fzfz}f_z+S_{Mxfz}[d_yf_z-d_zf_y]+S_{Myfz}[d_zf_x-d_xf_z]+S_{Mzfz}[d_xf_y-d_yf_x]$ 4) Equations for Recalculation of Moment Sensitivity Terms $v_{mx}=S_{fxmx}f_x+S_{fymx}f_y+S_{fzmx}f_z+S_{Mxmx}[d_yf_z-d_zf_y]+S_{Mymy}[d_zf_x-d_xf_z]+S_{Mzmx}[d_xf_y-d_yf_x]$ $v_{my}=S_{fxmy}f_x+S_{fymy}f_y+S_{fzmy}f_z+S_{Mxmy}[d_yf_z-d_zf_y]+S_{Mymy}[d_zf_x-d_xf_z]+S_{Mzmy}[d_xf_y-d_yf_x]$ $V_{mz}=S_{fxmz}f_x+S_{fymz}f_y+S_{fzmz}f_z+S_{Mxmz}[d_yf_z-d_zf_y]+S_{Mymz}[d_zf_x-d_xf_z]+S_{Mzmz}[d_xf_y-d_yf_x]$ 5) General Method for Least Squares Each of the outputs in 3 and 4 above will be solved with least squares approach. A minimum of six linearly independent equations must be developed by modifying loading conditions for forces and moments. The sets of equations take on the form shown in the following:

$$^1v_{fx} = S^1_{fxfx}f_x + S^1_{fyfx}f_y + S^1_{fzfx}f_z +$$
$$S^1_{Mxfx}[d_yf_z - d_zf_y] + S^1_{Myfx}[d_zf_x - d_xf_z] + S^1_{Mzfx}[d_xf_y - d_yf_x]$$

$$^2v_{ft} = S^2_{fxft}f_x + S^2_{fyfx}f_y + S^2_{fzfx}f_z + S^2_{Mxfx}[d_yf_z - d_zf_y] +$$
$$S^2_{Myfx}[d_zf_x - d_xf_z] + S^2_{Mzfx}[d_xf_y - d_yf_x]$$

$$\vdots$$

$$^6v_{fx} = S^6_{fxfx}f_x + S^6_{fyfx}f_y + S^6_{fzfx}f_z +$$
$$S^6_{Mxfx}[d_yf_z - d_zf_y] + S^6_{Myfx}[d_zf_x - d_xf_z] + S^6_{Mzfx}[d_xf_y - d_yf_x]$$

APPENDIX B

3-D GRID CALIBRATION PROCEDURE
The Mathematical Approach

In developing our calibration approach we first consider the effects of the moment cross talk. The sum of the moments for each axis is:

$m_0=0-f_1d_2+f_2d_1+T_0$ $m_1=f_0d_2+0-f_2d_0+T_1$ $m_2=-f_0d_1+f_1d_0+0+T_2$ (0.1)

However we assume that people do not have sticky feet and that they can not apply a pure couple or torque around the x and y axes so that:

$T_0=T_1=0$ (0.2)

Next we show that the output of channel Fx ($v_0$) is equal to the sum of the contributions of the three force inputs and three moment inputs each multiplied by some sensitivity. Similar reasoning and equations can be developed for all six channels.

$v_0 = s_{00}f_0 + s_{01}f_1 + s_{02}f_2 + s_{03}m_0 + s_{04}m_1 + s_{05}m_2$ (0.3)

$\vdots$

Substituting (0.1) into (0.3) gives the following:

$v_0=s_{00}f_0+s_{01}f_1+s_{02}f_2+s_{03}(-f_1d_2+f_2d_1)+s_{04}(f_0d_2-f_2d_0)+s_{05}(-f_0d_1+f_1d_0+T_2)$ $v_0=s_{00}f_0+s_{04}f_0d_2-s_{05}f_0d_1+s_{01}f_1+-s_{03}f_1d_2+s_{05}f_1d_0+s_{03}f_2d_1-s_{04}f_2d_0+s_{02}f_2+s_{05}T_2$ (0.4)

This upon simplification shows us that:

$v_0=(s_{00}+s_{04}d_2-s_{05}d_1)f_0+(s_{01}-s_{03}d_2+s_{05}d_0)f_1+(s_{02}+s_{03}d_1-s_{04}d_0)f_2+s_{05}T_2$ (0.5)

In other words the Fx output is dependent on the three applied forces and the applied torque $T_z$ ($T_3$) and the distance d of the point of force application to the origin of the force of the force plate reference frame. So a single aggregate cross talk term may be used at any given point to characterize the effects of moment and force cross talk. The remaining term $s_{05}$ represents the effect of pure Mz torque on the output. Under most circumstances $T_3$ is quite small and the resulting cross talk is negligible. The contribution of Mz resulting from moment of force is captured in the force cross talk terms.

Coming at the problem from our traditional way of thinking we have a 6×6 matrix relating platform loads to platform outputs as shown in (0.6) below.

$$S \equiv \begin{vmatrix} s_{00} & s_{01} & s_{02} & 0 & 0 & s_{05} \\ s_{10} & s_{11} & s_{12} & 0 & 0 & s_{15} \\ s_{20} & s_{21} & s_{22} & 0 & 0 & s_{25} \\ s_{30} & 0 & 0 & s_{33} & 0 & 0 \\ 0 & s_{41} & 0 & 0 & s_{44} & 0 \\ 0 & 0 & s_{52} & 0 & 0 & s_{55} \end{vmatrix} \quad (0.6)$$

The $s_{05}$, s15, s25 terms are the influence of the Mz moment acting on the force channels while the $s_{30}$, s41, s52 terms are the influence of forces acting on their collinear moment channels. The $s_{05}$, s15, s25 terms can be set to zero as these interactions are represented in the force to force terms as shown in equation (0.5). In other words an Fx moment may be caused by an Fz force acting at a distance dy from the x axis. Cross talk from this action will be represented in the Fz to Fx force to force cross talk term. The Mz term also includes pure torque and we chose to neglect this effect.

The $s_{30}$, s41, s52 force to moment terms may be significant as evidenced by the Fz to Mz cross talk shown in our dead weight testing.

$$S \equiv \begin{vmatrix} s_{00} & s_{01} & s_{02} & 0 & 0 & 0 \\ s_{10} & s_{11} & s_{12} & 0 & 0 & 0 \\ s_{20} & s_{21} & s_{22} & 0 & 0 & 0 \\ s_{30} & 0 & 0 & s_{33} & 0 & 0 \\ 0 & s_{41} & 0 & 0 & s_{44} & 0 \\ 0 & 0 & s_{52} & 0 & 0 & s_{55} \end{vmatrix} \quad (0.7)$$

If we approach the problem by developing the relationships for the outputs of all of the measurement channels we arrive at the six equations in (0.8).

$v_0=(s_{00}+s_{04}d_2-s_{05}d_1)f_0+(s_{01}-s_{03}d_2+s_{05}d_0)f_1+(s_{02}+s_{03}d_1-s_{04}d_0)f_2+s_{05}T_2$ $v_1=(s_{10}+s_{14}d_2-s_{15}d_1)f_0+(s_{11}-s_{13}d_2+s_{15}d_0)f_1+(s_{12}+s_{13}d_1-s_{14}d_0)f_2+s_{15}T_2$ $v_2=(s_{20}+s_{24}d_2-s_{25}d_1)f_0+(s_{21}-s_{23}d_2+s_{25}d_0)f_1+(s_{22}+s_{23}d_1-s_{24}d_0)f_2+s_{25}T_2$ $v_3=(s_{30}+s_{34}d_2-s_{35}d_1)f_0+(s_{31}-s_{33}d_2+s_{35}d_0)f_1+(s_{32}+s_{33}d_1-s_{34}d_0)f_2+s_{35}T_2$ $$v_4=(s_{40}+s_{44}d_2-s_{45}d_1)f_0+(s_{41}-s_{43}d_2+s_{45}d_0)f_1+(s_{42}+s_{43}d_1-s_{44}d_0)f_2+s_{45}T_2$$

$$V_5=(s_{50}s_{54}d_2-s_{55}d_1)f_0+(s_{51}-s_{53}d_2+s_{55}d_0)f_1+(s_{52}+s_{53}d_1-s_{54}d_0)f_2+s_{55}T_2 \quad (0.8)$$

First we observe that all forces are constrained to act on the top surface of the platform therefore $d_2$ is known. Given $d_2$ then the system of equations in (0.8) represents six equations in six unknowns, $f_0$, $f_1$, $f_2$, $T_2$, $d_0$, and $d_1$.

All of the coefficients for the force terms in equations (0.8) are dependent on one or both of $d_0$ and $d_1$. Our thesis is that by developing these coefficients for a sufficiently fine grid (or interpolation node points) across the plane (the surface of the platform) represented by $d_0$ and $d_1$ we greatly improve platform performance in terms or reduced cross talk and perfection of COP measurement.

To do this we first develop a matrix of sensitivities to principle loads using linear regression on all calibration data across all nodes and calibration loads. The resulting regression line slopes represent the best first estimate of sensitivity across all of the calibrated conditions. The remainder of the matrix terms are assumed to be zero as shown in equation (0.9).

$$SE \equiv \begin{vmatrix} s_{00} & 0 & 0 & 0 & 0 & 0 \\ 0 & s_{11} & 0 & 0 & 0 & 0 \\ 0 & 0 & s_{22} & 0 & 0 & 0 \\ 0 & 0 & 0 & s_{33} & 0 & 0 \\ 0 & 0 & 0 & 0 & s_{44} & 0 \\ 0 & 0 & 0 & 0 & 0 & s_{55} \end{vmatrix} \quad (0.9)$$

If we substitute the estimated sensitivities into equations of (0.8) we get the following set of equations.

$$v_0=(se_{00})f_0+(0)f_1+(0)f_2+s_{05}T_2$$
$$v_1=(0)f_0+(se_{11})f_1+(0)f_2+s_{15}T_2$$
$$v_2=(0)f_0+(0)f_1+(se_{22})f_2+s_{25}T_2$$
$$v_3=(0)f_0+(-se_{33}d_2)f_1+(se_{33}d_1)f_2+s_{35}T_2$$
$$v_4=(se_{44}d_2)f_0+(0)f_1+(-se_{44}d_0)f_2+s_{45}T_2$$
$$v_5=(-se_{55}d_1)f_0+(se_{55}d_0)f_1+(0)f_2+s_{55}T_2 \quad (0.10)$$

Equations (0.10) can be further simplified by assuming the cross talk terms for $T_2$ to be negligible so we get:

$$v_0=(se_{00})f_0$$
$$v_1=(se_{11})f_1$$
$$v_2=(se_{22})f_2$$
$$v_3=(-se_{33}d_2)f_1+(se_{33}d_1)f_2$$
$$v_4=(se_{44}d_2)f_0+(-se_{44}d_0)f_2$$
$$v_5=(-se_{55}d_1)f_0+(se_{55}d_0)f_1+s_{55}T_2 \quad (0.11)$$

The first three equations can be solved directly for f while the last three represent three equations in three unknowns $d_0$, $d_1$, and $T_2$ which can be solved by substitution.

Thus we arrive at our first estimate of load and the point of load application which are then used to either look up or interpolate a set of coefficients for more exact solution of the problem.

$$v_0 = s_{00}f_0 + s_{01}f_1 + s_{02}f_2 \quad (0.12)$$
$$v_1 = s_{10}f_0 + s_{11}f_1 + s_{12}f_2$$
$$v_2 = s_{20}f_0 + s_{21}f_1 + s_{22}f_2$$

$$S \equiv \begin{vmatrix} s_{00} & s_{01} & s_{02} \\ s_{10} & s_{11} & s_{12} \\ s_{20} & s_{21} & s_{22} \end{vmatrix} \quad (0.13)$$

$$f = S^{-1} v^F \quad (0.14)$$

However (0.14) represents a set of 6 equations in 9 unknowns. Each of the applied loading conditions with principle components along the principle axes represents a nearly orthogonal (and hence linearly independent) condition.

So nine equations may be developed for the three loading conditions. Three different loading conditions tested for each load point, $f^1$, $f^2$ and $f^3$ result in corresponding outputs $v^{1F}$, $v^{2F}$ and $v^{3F}$. The corresponding equations are shown in (0.15)(0.16) and (0.17)

$$v_0^{1F}=S_{00}f_0^1+S_{01}f_1^1+S_{02}f_2^1$$
$$v_0^{2F}=S_{00}f_0^2+S_{01}f_1^2+S_{02}f_2^2$$
$$v_0^{3F}=S_{00}f_0^3+S_{01}f_1^3+S_{02}f_2^3 \quad (0.15)$$
$$v_1^{1F}=S_{10}f_0^1+S_{11}f_1^1+S_{12}f_2^1$$
$$v_1^{2F}=S_{10}f_0^2+s_{11}f_1^2+s_{22}f_2^2$$
$$v_1^{3F}=S_{10}f_0^3+S_{11}f_1^3+S_{12}f_2^3 \quad (0.16)$$
$$v_2^{1F}=S_{20}f_0^1+S_{21}f_1^1+S_{22}f_2^1$$
$$v_2^{2F}=S_{20}f_0^2+S_{21}f_1^2+s_{22}f_2^2$$
$$v_2^{3F}=S_{20}f_0^3+S_{21}f_1^3+S_{22}f_2^3 \quad (0.17)$$

These equations are solved by least squares analysis using LinPack.

The next step is to calculate the main diagonal Mx and My sensitivities ($S_{33}$ and $S_{44}$) from the known moment outputs and known position and load. We should also calculate $S_{52}$ at this point.

To calculate $S_{33}$ and $S_{44}$ we must first determine the x and y axes offsets. The axes offsets are the difference between the zero moment positions and the geometrical coordinate system axes. These offsets are calculated directly from the outputs resulting from Fz loads applied at the geometrical coordinate system axes, that is when either $d_x$ or $d_y$ are zero.

We use the estimated moment sensitivities $se_{33}$ and $se_{44}$ to determine the offsets $q_0$ and $q_1$ as follows:

$$q_1=(-1/se_{33})v_3/f_2$$
$$q_0=(1/se_{44})v_4/f_2 \quad (0.18)$$

In equation (0.18) $v_3$, $v_4$ and $f_2$ correspond to on axis loading where either $d_x$ or $d_y$ is zero.

$$s_{33}=v_3/(f_2(d_1-q_1))$$
$$s_{44}=-v_4/(f_2(d_0-q_0)) \quad (0.19)$$

Moving on to the moments which are shown in equation (0.20).

$$v_3^{2F}=s_{30}f_0^{2F}+s_{33}f_2^{2F}d_1^{2F}-s_{33}f_1^{2F}d_{02}^{2F}$$
$$v_3^{4F}=s_{30}f_0^{4F}+s_{33}f_2^{4F}d_1^{4F}-s_{33}f_1^{4F}d_{02}^{4F}$$

$$d_{02}{}^{4F}=d_{02}{}^{2F}c+$$

$$v_4{}^{1F}=s_{41}f_1{}^{1F}-s_{44}f_2{}^{1F}d_0{}^{1F}+s_{44}f_0{}^{1F}d_{12}{}^{1F}$$

$$v_4{}^{5F}=s_{41}f_1{}^{5F}-s_{44}f_2{}^{5F}d_0{}^{5F}+s_{44}f_0{}^{5F}d_{12}{}^{5F}$$

$$d_{12}{}^{5F}=d_{12}{}^{1F}c+$$

$$v_5{}^{1F}=s_{52}f_2{}^{1F}+s_{55}f_1{}^{1F}d_0{}^{1F}-s_{55}f_0{}^{1F}d_1{}^{1F}+s_{55}T_2{}^{1F}$$

$$v_5{}^{6F}=S_{52}f_2{}^{6F}+s_{55}f_1{}^{6F}d_0{}^{6F}-s_{55}f_0{}^{6F}d_1{}^{6F}+s_{55}T_2{}^{6F} \qquad (0.20)$$

The set of equations (0.20) may be solved using least squares technique or by substitution leading to the cross talk sensitivities $s_{30}$, $s_{41}$ and offset distances $d_{02}$ and $d_{12}$.

To provide corrected analog outputs the results from equations (0.14) and (0.20) must be rescaled using the desired sensitivity values. Suppose we wish to rescale to the original estimated sensitivities, SE, then:

$$v=SEf \qquad (0.21)$$

Rescaling the moments requires that the desired $d_2$ ($d_z$) be chosen, and that $se_{33}$, $se_{44}$ and $se_{55}$ be substituted for $s_{33}$, $s_{44}$ and $s_{55}$ in equations (0.20). Note that the error offsets terms are omitted from the final output calculations as these have been accommodated in the initial solution for d.

$$v_3=se_{33}f_2d_1-se_{33}f_1d_z$$

$$v_4=-se_{44}f_2d_0+se_{44}f_0d_z$$

$$v_5=se_{55}f_1d_0-se_{55}f_0d_1+s_{55}T_2 \qquad (0.22)$$

Equations (0.1) through (0.22) detail the basic calibration approach. To accomplish this, coefficients of matrix SE of equation (0.9) and the matrix S of the equation (0.7) must be developed for each calibration node on a grid of points spanning the top surface of the platform. The nature of the S matrix allows us to decompose it into a 3×3 matrix of (0.13) and a set of coefficients shown in (0.20). The S matrix may be inverted by normal means yielding $S^{-1}$ which can be used to determine the vector of applied force, f. In turn, the components of f along with the S coefficient terms for the moments are used to solve the system of moment equations.

What is claimed is:

1. A method for calibrating a force platform comprising:
providing a force platform and applying a grid of points on a top surface of the force platform via a computing device, wherein said top surface extends along an X-axis, and along a Y-axis of said force platform;
applying p known loads on each of the grid points of the top surface along a Z-axis being perpendicular to said X and Y axes and along said X and Y axes;
taking multipoint measurements at each grid point and for each applied known load along said X, Y and Z axes;
generating six measured output signals, exact position coordinates and applied known load magnitude for each grid point;
assembling an array of six equations with six unknowns for each grid point and applied known load;
solving the assembled equations and deriving a position and load specific calibration matrix for each grid point and applied known load; and
entering the derived position and load specific calibration matrices for all grid points in a calibration table and storing the calibration table in a non-volatile memory.

2. The method of claim 1 wherein said p known loads are applied via a 3-D Cartesian load apparatus.

3. The method of claim 1 wherein said applied p known loads comprise magnitudes in the range of zero to Full Scale Capacity (FSC) at increments of 10%.

4. The method of claim 1, wherein said grid of points comprises n and m points extending along said X and said Y axis, respectively, and wherein said n and m points comprise values in the range of 2 to 20.

5. The method of claim 1, wherein said six measured output signals comprise three force components Fx, Fy, Fz and three moment components Mx, My, Mz.

6. The method of claim 1, further comprising providing an estimate algorithm and storing a global platform calibration matrix in said non-volatile memory, wherein the estimate algorithm is configured to generate first estimates of magnitude and position of an unknown applied load on the force platform by applying the global platform calibration matrix onto measured platform outputs for the unknown applied load.

7. The method of claim 6, wherein the first estimates of magnitude and position of the unknown applied load are used to determine a position and load specific calibration matrix in the calibration table.

8. The method of claim 7, further comprising generating accurate measures of the magnitude and position of the applied unknown load by applying the determined position and load specific calibration matrix onto the measured platform outputs for the unknown load.

9. The method of claim 1, further comprising verifying said derived position and load specific calibration matrices by applying NIST traceable dead weights onto the top surface grid points.

10. The method of claim 1, further comprising measuring secondary characteristics at eight grid points using a calibration protocol.

11. A system for calibrating a force platform comprising:
a force platform;
a computing device comprising a processor and a memory storing instructions that when executed cause to apply a grid of points on a top surface of the force platform, wherein said top surface extends along an X-axis, and along a Y-axis of said force platform;
a 3-D Cartesian load apparatus comprising an actuator and a memory storing instructions that when executed cause to apply p known loads on each of the grid points of the top surface along a Z-axis being perpendicular to said X and Y axes and along said X and Y axes;
a sensor configured to take multipoint measurements at each grid point and for each applied known load along said X, Y and Z axes and to generate six measured output signals, exact position coordinates and applied known load magnitude for each grid point;
an algorithm for solving an assembled array of six equations with six unknowns for each grid point and applied known load and for deriving a position and load specific calibration matrix for each grid point and applied known load; and
a non-volatile memory configured to store a calibration table comprising the derived position and load specific calibration matrices for all grid points.

12. The system of claim 11 wherein said applied p known loads comprise magnitudes in the range of zero to Full Scale Capacity (FSC) at increments of 10%.

13. The system of claim 11, wherein said grid of points comprises n and m points extending along said X and said Y axis, respectively, and wherein said n and in points comprise values in the range of 2 to 20.

14. The system of claim 11, wherein said six measured output signals comprise three force components Fx, Fy, Fz and three moment components Mx, My, Mz.

15. The system of claim 11, further comprising an estimate algorithm and a global platform calibration matrix, wherein the estimate algorithm is configured to generate first estimates of magnitude and position of an unknown applied load on the force platform by applying the global platform calibration matrix onto measured platform outputs for the unknown applied load.

16. The system of claim 15, wherein the first estimates of magnitude and position of the unknown applied load are used to determine a position and load specific calibration matrix in the calibration table.

17. The system of claim 16, further comprising a correction algorithm generating accurate measures of the magnitude and position of the applied unknown load by applying the determined position and load specific calibration matrix onto the measured platform outputs for the unknown load.

* * * * *